United States Patent
Bathiche et al.

(10) Patent No.: US 9,216,133 B2
(45) Date of Patent: Dec. 22, 2015

(54) USING A 3D DISPLAY TO TRAIN A WEAK EYE

(71) Applicant: Elwha LLC, Bellevue, WA (US)

(72) Inventors: Steven Bathiche, Kirkland, WA (US); Alistair K. Chan, Bainbridge Island, WA (US); William Gates, Medina, WA (US); Roderick A. Hyde, Redmond, WA (US); Edward K. Y. Jung, Bellevue, WA (US); Jordin T. Kare, Seattle, WA (US); Jaron Lanier, Sausalito, CA (US); John L. Manferdelli, San Francisco, CA (US); Clarence T. Tegreene, Mercer Island, WA (US); David B. Tuckerman, Lafayette, CA (US); Charles Whitmer, North Bend, WA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 55 days.

(21) Appl. No.: 13/743,168

(22) Filed: Jan. 16, 2013

(65) Prior Publication Data
US 2014/0198297 A1 Jul. 17, 2014

(51) Int. Cl.
*A61B 3/00* (2006.01)
*A61B 3/08* (2006.01)
*A61H 5/00* (2006.01)
(Continued)

(52) U.S. Cl.
CPC ............... *A61H 5/005* (2013.01); *A61B 3/113* (2013.01); *G02B 27/0093* (2013.01); *A61H 2201/5007* (2013.01); *A61H 2201/5048* (2013.01); *A61H 2201/5058* (2013.01); *A61H 2201/5064* (2013.01); *A61H 2201/5079* (2013.01);
(Continued)

(58) Field of Classification Search
CPC ........ A61B 3/005; A61B 3/022; A61B 3/024; A61B 3/032; A61B 3/08; A61B 3/113; A61H 5/005; A61H 5/05; A61H 2201/5043; A63F 2300/301; A63F 13/00; G06F 3/013; G06F 3/048; H04N 13/04
USPC ............ 351/201, 203, 209, 246, 210; 348/54; 345/156, 419; 715/801; 463/32
See application file for complete search history.

(56) References Cited

U.S. PATENT DOCUMENTS 6,511,175 B2 * 1/2003 Hay et al. ........................ 351/45
2001/0050754 A1 12/2001 Hay et al.
(Continued)

OTHER PUBLICATIONS

Gargantini, Angelo. "Using Stereoscopic 3D Technologies for the Diagnosis and Treatment of Amblyopia in Children". Computing Research Repository, 2011. https://web.archive.org/web/20111113221316/http://www.informatik.uni-trier.de/~ley/db/journals/corr/corr1109.html, arXiv:1109.6288 [cs.HC].*
(Continued)

*Primary Examiner* — Zachary Wilkes
*Assistant Examiner* — Collin X Beatty
(74) *Attorney, Agent, or Firm* — Foley & Lardner LLP

(57) ABSTRACT

A method for treating a weak viewer-eye includes the steps of receiving eye-strength data indicative of an eye-strength of the weak viewer-eye and causing a 3D display system to vary, in accordance with the eye-strength of the weak viewer-eye, display characteristics of a perspective that the 3D display system displays.

34 Claims, 13 Drawing Sheets

(51) Int. Cl.
  *A61B 3/113* (2006.01)
  *G02B 27/00* (2006.01)

(52) U.S. Cl.
  CPC . *A61H2201/5084* (2013.01); *A61H 2201/5092* (2013.01); *A61H 2201/5097* (2013.01)

(56) References Cited

U.S. PATENT DOCUMENTS

| | | | | |
|---|---|---|---|---|
| 2006/0087618 | A1* | 4/2006 | Smart et al. | 351/222 |
| 2007/0200927 | A1* | 8/2007 | Krenik | 348/47 |
| 2010/0201942 | A1 | 8/2010 | Hess et al. | |
| 2010/0283969 | A1* | 11/2010 | Cooperstock et al. | 351/201 |
| 2011/0006978 | A1* | 1/2011 | Yuan | 345/156 |
| 2011/0164122 | A1 | 7/2011 | Hardacker | |
| 2011/0304818 | A1* | 12/2011 | Reichow et al. | 351/201 |
| 2012/0046143 | A1* | 2/2012 | Bell | 482/1 |
| 2012/0069296 | A1* | 3/2012 | Li et al. | 351/201 |
| 2012/0075586 | A1* | 3/2012 | Kirschen et al. | 351/239 |
| 2012/0082353 | A1* | 4/2012 | Kelusky et al. | 382/128 |
| 2012/0092618 | A1* | 4/2012 | Yoo et al. | 351/209 |
| 2012/0105609 | A1* | 5/2012 | Qi | 348/54 |
| 2012/0127426 | A1* | 5/2012 | Backus et al. | 351/203 |
| 2012/0147328 | A1* | 6/2012 | Yahav | 351/210 |
| 2012/0154751 | A1* | 6/2012 | Pelah et al. | 351/224 |
| 2012/0179076 | A1* | 7/2012 | Bavelier et al. | 601/37 |
| 2012/0190448 | A1* | 7/2012 | Larsen et al. | 463/36 |
| 2012/0190968 | A1* | 7/2012 | Raber | 600/411 |
| 2012/0249951 | A1* | 10/2012 | Hirayama | 351/201 |
| 2012/0300173 | A1* | 11/2012 | Reichow et al. | 351/203 |
| 2012/0307203 | A1* | 12/2012 | Vendel et al. | 351/201 |
| 2012/0307204 | A1* | 12/2012 | Trachtman | 351/203 |
| 2012/0320336 | A1* | 12/2012 | Kapoula et al. | 351/203 |
| 2012/0322588 | A1* | 12/2012 | Khaderi | 473/458 |
| 2014/0293226 | A1* | 10/2014 | Hainzl et al. | 351/210 |
| 2015/0070349 | A1* | 3/2015 | Shinomiya et al. | 345/419 |

OTHER PUBLICATIONS

Newton, James. "3DS May Be Beneficial to Young Players' Eyes, Actually". Nintendolife.com, Jan. 6, 2011. https://web.archive.org/web/20110108035609/http://3ds.nintendolife.com/news/2011/01/3ds_may_be_beneficial_to_young_players_eyes_actually.*

* cited by examiner

USING A 3D DISPLAY TO TRAIN A WEAK EYE

BACKGROUND

Many people suffer from vision disorders in which one eye is weaker than the other, leading to problems with binocular vision, motion-perception, depth perception, and spatial acuity. If left untreated, a person's brain may increasingly rely on the stronger eye for information, further reducing the effectiveness of the weaker eye until, in some cases, the weak eye becomes non-functional.

To treat such disorders, a physician may block or obscure the view of the patient's stronger eye to make the weaker-eye work harder (i.e., force the person to rely more on the weak eye). With his or her vision obscured, the patient may engage in activities in which good vision is necessary for a prescribed period of time, in order to train the weaker eye. The improvement in eye strength of the patient's weak eye is generally proportional to the amount of time that the patient spends training the weak eye. Because such training takes many hours to effect a change in the patient, the training routine typically takes place under the patient's discretion and without professional supervision. One drawback of such an approach is that a patient may occasionally avoid or forget the training.

3D display systems have existed in a variety of forms for many years. Generally, these systems convey a sense of depth by presenting slightly different perspectives of the same image to each of a viewer's eyes. One typical 3D display process involves presenting two superimposed images simultaneously from a single display screen with the superimposed images modified to be separable from each other through the use of optical filters. Different filters may then be placed in front of each of a viewer's eyes (e.g., in 3D glasses) so that the viewer sees one image with the left eye and a different image with the right eye. If the two images are slightly offset views of the same scene, the viewer will instinctively combine the images into a 3D representation of the scene. Conventional systems have employed color filters (such as red/cyan tinted glasses), type of light-polarization (i.e., planar, elliptical, linear, etc.), or polarization angle as characteristics for filtering images using filters placed near to the eyes.

More recently, displays have been developed that can present 3D images without placing filters near the eyes. Such systems, known as autostereoscopic displays, hold tremendous potential for bringing 3D display technology to a variety of untapped applications. Emerging uses for 3D technology include medical imaging, entertainment, diagnostics, education, and defense, among many other fields.

SUMMARY

In one exemplary embodiment, a method for treating a weak viewer-eye involves receiving eye-strength data indicative of an eye-strength of the weak viewer-eye. The method also involves causing a 3D display system to vary, in accordance with the eye-strength of the weak viewer-eye, display characteristics of a perspective that the 3D display system displays.

In another exemplary embodiment, a display-control device includes a computer-readable medium with program instructions stored thereon that are executable by an included processor to cause the processor to perform certain functions. The functions include receiving eye-strength data representative of the eye-strength of a set of viewer-eyes that includes a weak viewer-eye. The functions further include causing a 3D display system to vary, in accordance with the eye-strength of the weak viewer-eye, the display characteristics of a perspective that the 3D display system displays.

In yet another exemplary embodiment, a non-transitory computer-readable medium contains program instructions executable by a processor to cause a display-control device to perform certain functions. The functions include receiving eye-strength data representative of an eye-strength of a weak viewer-eye and causing a 3D display system to vary, in accordance with the eye strength of the weak viewer-eye, display characteristics of a perspective that the 3D display system displays.

In a further exemplary embodiment, a 3D display system includes a 3D display screen, a processor, and program instructions stored on a computer-readable medium. The 3D display screen is configured to display multiple perspectives of an image. The program instructions are executable to cause the processor to receive eye-strength data representative of an eye-strength of a weak viewer-eye and vary display characteristics of a perspective of the image in accordance with the eye-strength of the weak viewer-eye.

In another exemplary embodiment, an exemplary method involves causing a 3D display system to display a first and second perspective of an image, with the first perspective intended for a first viewer-eye and the second perspective intended for a second viewer-eye. The method also involves determining an eye-strength of the first viewer-eye with respect to the second viewer-eye and varying display characteristics of the first or second perspective of the image based on the determined eye-strength of the first viewer-eye.

In still another exemplary embodiment, an eye-monitoring system for controlling a 3D display system includes an eye sensor configured to detect characteristics of a viewer's eyes and a display-system interface connecting the eye-monitoring system to the 3D display system. The eye-monitoring system also includes control circuitry configured to generate eye-strength data from the characteristics detected by the eye sensor.

The foregoing is a summary and thus by necessity contains simplifications, generalizations and omissions of detail. Consequently, those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Referring generally to the figures, systems and methods for using a 3D display system to diagnose and/or treat weakness in one of a viewer's eyes are shown and described. For example, to treat such eye-weakness, a 3D display system may provide an enhanced image to the viewer's weak eye and/or provide a diminished or obscured image to the viewer's dominant eye. In this way, the viewer's weak eye can be trained without the viewer needing to physically obstruct the dominant eye. Although the dominant viewer-eye may also herein be referred to as the strong viewer-eye or strong eye, the viewer's dominant eye need not be particularly strong. Additionally, displaying a perspective to a "viewer-eye," a "weak eye," a "strong eye," or a "dominant eye" need not require that a viewer be actually watching. Rather, the perspective is displayed towards what the display system interprets as a "viewer-eye," etc.

Example Device and System Architecture

Figure 1:
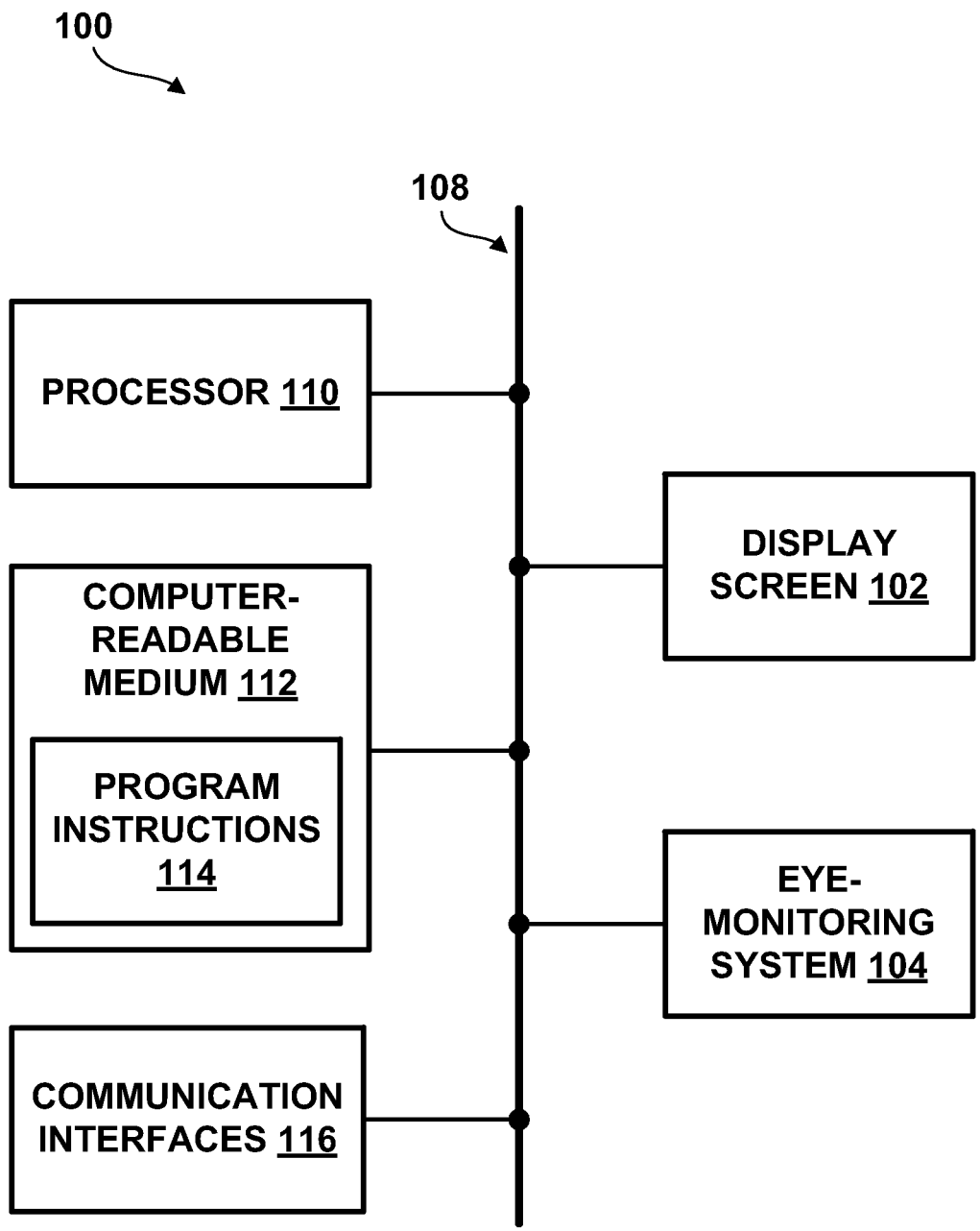
FIG. 1 is a schematic design of a 3D display system according to an exemplary embodiment.

FIG. 1 is a schematic of a display system 100 according to an exemplary embodiment. As shown, display system 100 includes display screen 102, eye-monitoring system 104, processor 110, computer-readable medium (CRM) 112, and communication interfaces 116, each coupled to system bus 108. As further shown in FIG. 1, program instructions 114 are stored on CRM 112. Some embodiments may not include all the elements shown in FIG. 1 and/or may include additional elements not shown in the example system of FIG. 1.

System bus 108 is shown in FIG. 1 as a single connection for simplicity. However, elements in an exemplary system may connect through a variety of interfaces, communication paths, and networking elements. Connections may be wired, wireless, optical, mechanical, or any other connector type.

I. Display Screen

Display screen 102 may include one or more light sources and a variety of other optical features for presenting images. Light sources may include, for example, light emitting diodes, other electroluminescent components, incandescent light sources, gas discharge sources, lasers, electron emission sources, and/or quantum dot sources, among other existing and future light-source technologies. In an example display screen, sets of light sources may be organized into arrays and other such groupings in order to form complex images or patterns. In such an arrangement, each light source may behave as an individual illuminated location (sometimes referred to as a pixel) on a larger display screen. In other arrangements, single light sources may illuminate several pixels.

The light-producing elements of display screen 102 may connect to various display-control interfaces. A control unit that signals the screen elements to manage the display may take various forms, as will be discussed in a later section. In some arrangements, a controller may independently signal each pixel through an individual electrical or optical connection.

In other arrangements, a set of pixels may interface collectively with a control unit. For example, three differently colored light sources may be signaled collectively so that the combined output is a particular color. As another example, several superimposed signals may be transmitted to a set of pixels with each signal intended for one of the pixels. At the display screen, the combined signal may be filtered into its constituent parts and each signal sent to its intended pixel.

In still other arrangements, a controller may control a single light source in order to provide light for multiple pixels. For example, the light output from a single light source may be expanded, split, and/or filtered to produce multiple simultaneously displayed pixels. As another example, a source may be configured to illuminate each of a set of display-locations on a display screen sequentially, cycling through the locations and providing light to each location one at a time. Other example control arrangements may also be used.

Optical features other than light sources may include, for example, lenses, mirrors, beam-splitters, liquid crystals, electronic ink, baffles, filters, polarizers, and/or waveguides. As one example, a lenticular display-screen may include arrays of small convex lenses (called lenticules) arranged above an underlying image in such a way as to magnify different portions of the underlying image depending on the angle from which the image is viewed. In particular, lenticules and underlying images may be designed so that two or more entirely different images are presented when the screen is viewed from specific angles. As will be discussed, optical deflectors may also be used to change the direction of light output from display screen 102. Other examples are possible.

In some implementations, optical elements other than light sources may be controllable through mechanical, electrical, acoustic, optical, or other stimuli. In such cases, a control unit may communicate either independently or collectively with controllable elements in much the same way that the control unit may communicate with arrays of pixels.

As a particular example, display system 100 may use controllable optical-deflectors to adjust the direction of light output from display screen 102. Because, in some cases, the direction of narrow (i.e., low divergence) beams of light may be adjusted more effectively than higher-divergence light sources, such an implementation may be termed a "beam-to-viewer" system. The direction of the light, for instance, may be adjusted so that a particular image is directed to one viewer's eye. In such a system, display screen 102 may direct images associated with a right-eye view towards a viewer's right eye and images associated with a left-eye view to the viewer's left eye. In other systems, the direction that a light source emits light may be controlled directly without actively deflecting the light. For example, a system may physically turn light sources to change the direction.

Figure 2A:
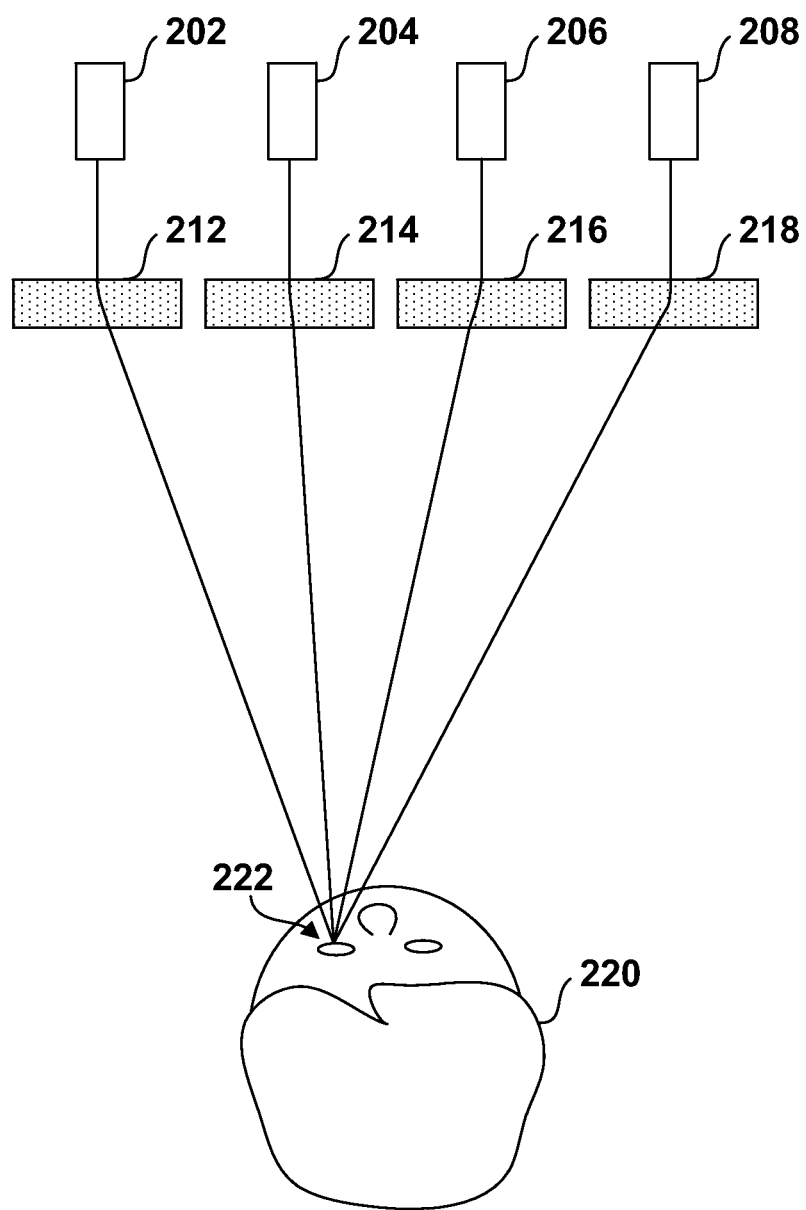
FIG. 2A is a light-ray diagram of an example display system in use.
Figure 2B:
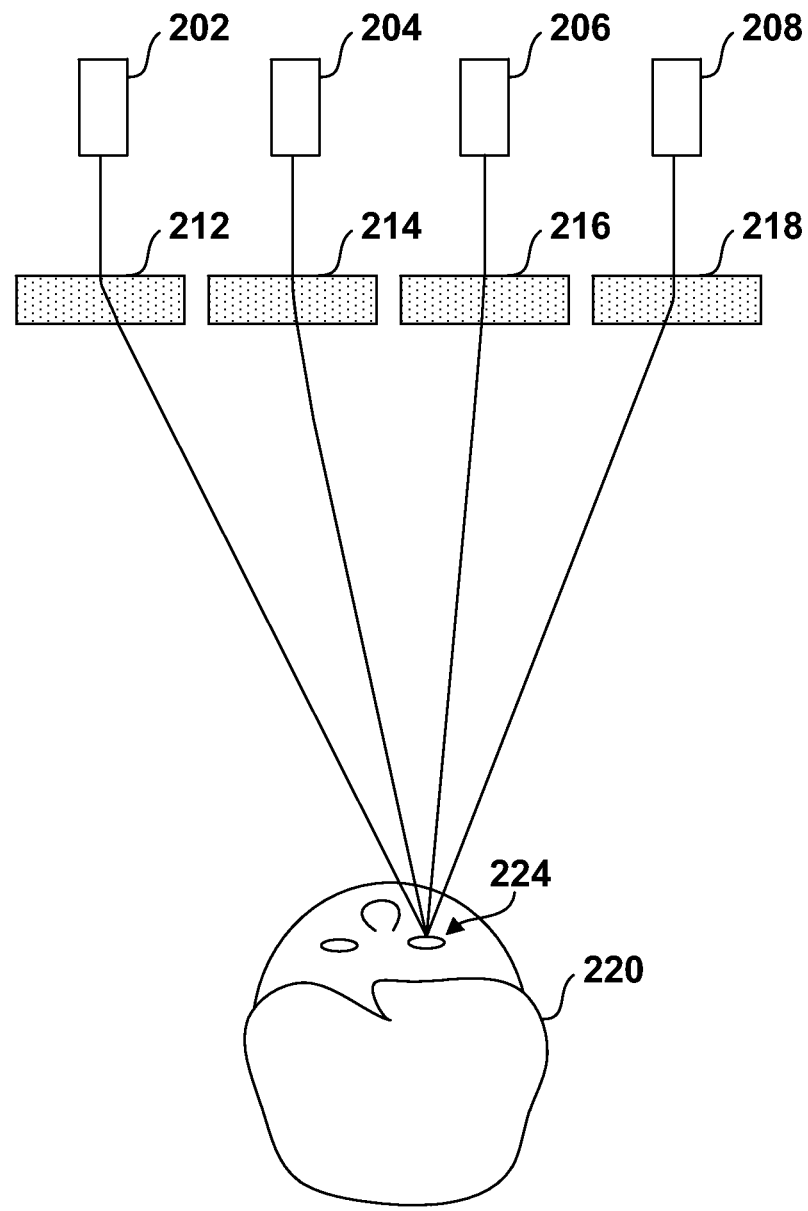
FIG. 2B is a light-ray diagram of an example display system in use.

FIGS. 2A-2D are ray diagrams illustrating example beam-to-viewer display systems in use. FIG. 2A shows light rays deflecting towards a left viewer-eye 222 at a first time-step and FIG. 2B shows light rays deflecting towards a right viewer eye 224 at a second time-step. Although the embodiment shown alternates between displaying one view and another, other beam-to-viewer systems may send different beams simultaneously to each of a viewer's eyes. As shown in FIG. 2A, light is emitted from light sources 202, 204, 206, and 208, through optical deflectors 212, 214, 216, and 218 towards the left viewer-eye 222 of viewer 220. Although deflectors 212-218 are shown as separate devices in FIGS. 2A-B, an example optical-deflection system may alternatively use a single-device deflection system.

As shown in FIG. 2B, at a second time-step, light sources 202, 204, 206, and 208 continue to emit light rays through optical deflectors 212, 214, 216, and 218. In contrast to the first time-step, however, optical deflectors 212-218 deflect light towards the right viewer-eye 224 of viewer 220 during the second time-step. In an example process, the light may alternate between the first and second time-steps. The time-step shown in FIG. 2A is termed the "first" time-step only to differentiate it from the second time-step. Throughout the present disclosure, no intended order of operations should be implied from the labels "first" or "second" unless otherwise specified.

Figure 2C:
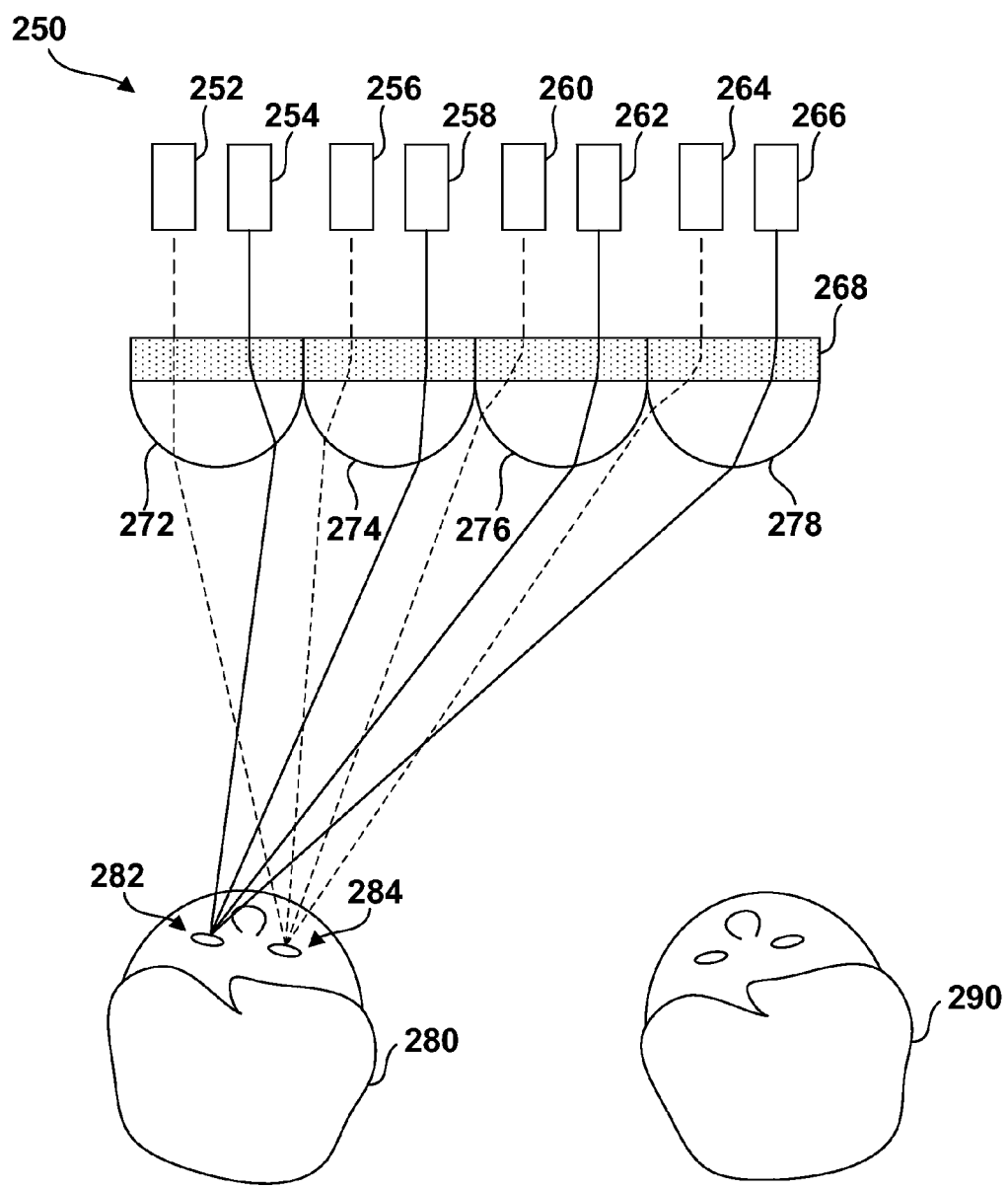
FIG. 2C is a light-ray diagram of an example display system in use.
Figure 2D:
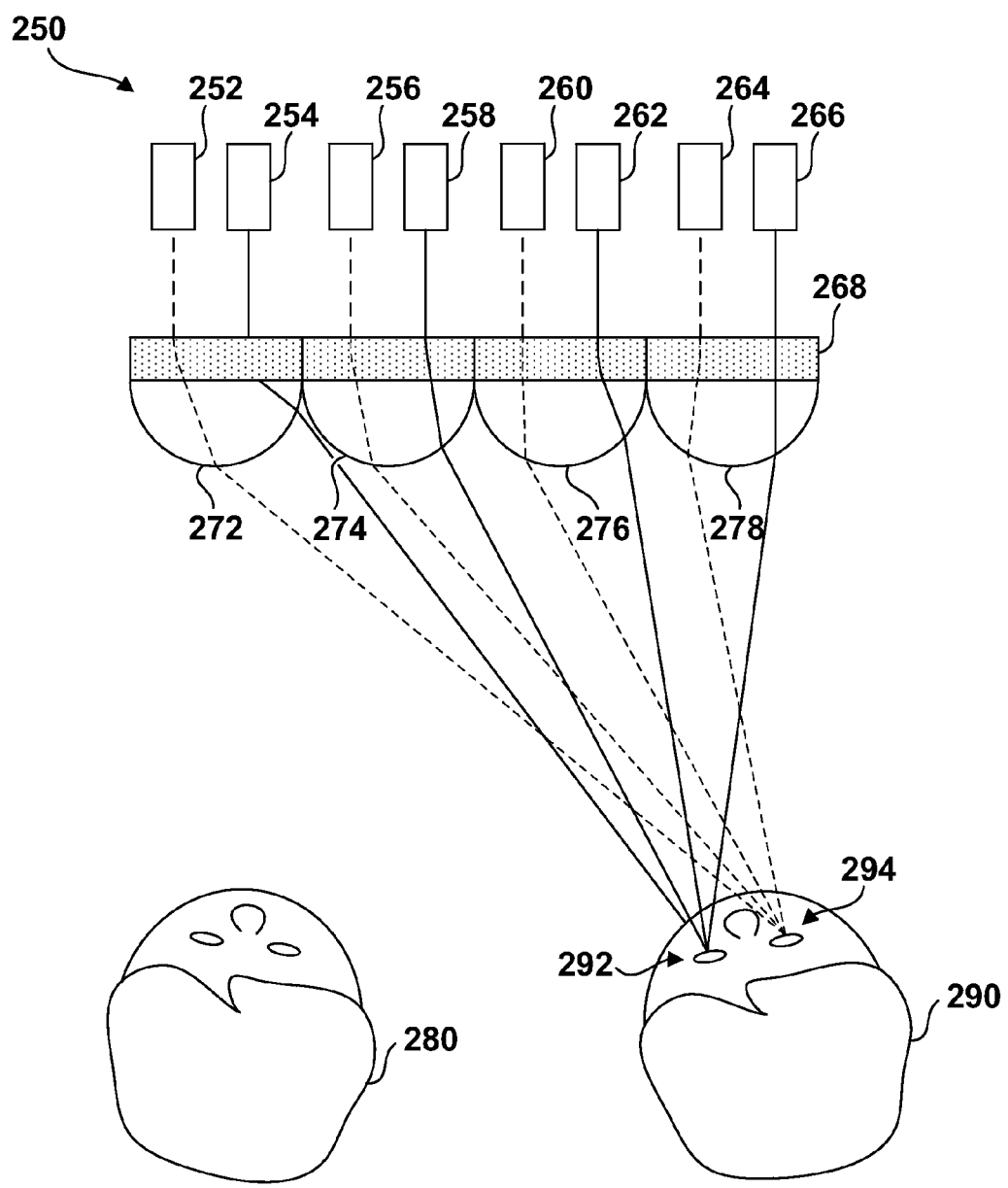
FIG. 2D is a light-ray diagram of an example display system in use.

FIGS. 2C and 2D are light-ray diagrams showing another beam-to-viewer system in use. In particular, the light rays are deflected to the eyes of two viewers in an alternating sequence. In other implementations, a beam-to-viewer system may display to both viewers simultaneously. The particular sequence shown involves displaying both the left and right views of the 3D images to viewer 280 at a first time-step (shown in FIG. 2C) and displaying both the left and right views of the 3D images to viewer 290 at a second time-step. As shown, at the first time-step, light sources 254, 258, 262, and 266 emit light rays (shown as solid lines) representing a left-eye view through optical deflector 268 and lenticules 272, 274, 276, and 278 towards the left viewer-eye 282 of viewer 280. Also at the first time-step, light sources 252, 256, 260, and 264 emit light rays (shown as dashed lines) representing a right-eye view through optical deflector 268 and lenticules 272, 274, 276, and 278 towards the right viewer-eye 282 of viewer 280. Although optical deflector 268 is shown as a single segmented deflector, other embodiments may include separate deflectors for each light source or lenticule.

At the second time-step, FIG. 2D shows that light sources 252-266 emit portions of the left and right views in the same way as in the first time-step. However, the light rays are deflected by deflector 268 so that, after passing through lenticules 272-278, the light rays are directed to viewer 290's left viewer-eye 292 and right viewer-eye 294. Other implementations and procedures may be used as well to display 3D images to two or more viewers.

In addition to beam-to-viewer systems, a 3D display screen may use a variety of techniques to portray different images to different viewers. For instance, near-eye optical filters (e.g., 3D glasses) may be used to separate superimposed images. As another example, a system may use holographic displays, lenticular screens, parallax-barrier displays, or wiggle stereoscopy to present the pair of images. Although a 3D display screen 102 and a 3D display device 100 may be particularly used for displaying 3D images, these systems may also display 2D images. For example, if a 3D display system receives a 2D image or video, the system may display substantially the same image(s) for each perspective of the 2D image or video. Because system may vary the display characteristics, the perspectives may not be exactly the same.

II. Eye-Monitoring System

Eye-monitoring system 104 may also be included in or connected to display system 100. In some arrangements, eye-monitoring system 104 may be integral in the same device as display screen 102 and other elements. In other cases, eye-monitoring system 104 may communicate with other elements of the system, through an electrical, optical, or other communicative interface. In some cases, eye-monitoring system 104 may control itself, sending eye-strength and other data automatically. In other arrangements, a central controller may send control signaling eye-monitoring system 104 to initiate generation of eye-strength data.

Eye-monitoring system 104 may use a variety of sensors to generate eye-strength data. For example, a video-processing approach may involve capturing images in the direction that display screen 102 faces and analyzing the images to detect portions of the image that are representative of characteristics of a viewer-eye. As another example, reflection sensors may detect characteristics of viewer-eyes by sending optical or acoustic signals towards the eyes, measuring signals that are reflected back towards the sensor, and processing the reflected signals to detect eye-characteristics. In some optical reflection-sensor systems, the light may reflect off the surface of the eye. In other systems, the light may pass through portions of the eye and reflect off the back of the eye. In still other reflection-sensor systems, the light or sound waves may reflect off areas other than the eye itself (e.g., skin around the eye or other body features). In systems that detect multiple eye-characteristics, eye-monitoring system 104 may include various sensors and sensor-types to monitor the eyes.

In some implementations, eye-monitoring system 104 may be configured to generate new eye-strength data occasionally by determining a current eye-strength of the detected eyes and updating the eye-strength data with the most current data. For example, eye-monitoring system 104 may determine eye strength periodically, that is, at predefined time-intervals. In some cases, the time intervals between successive determination steps may be so brief as to create a substantially continuous reading of the eye strength. In other embodiments, eye-monitoring system 104 may determine eye strength in response to a particular signal. For example, eye-monitoring system 104 may receive movement data from one or more motion sensors and initiate an eye-strength determination procedure in response to receiving data indicating a sufficiently large movement in the viewing area of display screen 102. Such a technique may help the system to recognize when a particular viewer stops watching, so that the system may stop varying display characteristics.

The strength of a viewer-eye may be determined in a variety of ways. In some systems, eye-monitoring system 104 may internally process sensor readings to determine the eye-strength of the viewer-eye. In other systems, eye-monitoring system 104 may send data to a centralized processor for processing and analysis to determine eye strength. In still other systems, eye-strength data may be accessed from storage or input directly, so that no eye-monitoring system is used.

In addition to eye strength, eye-monitoring system 104 may determine and report other information about viewer-eyes. For example, eye-monitoring system 104 may report the location of detected eyes. Such eye-location data may help beam-to-viewer systems to direct the light towards the viewer-eyes or other 3D displays to determine which viewer-eye (e.g., right or left) was viewing each pixel of the display. As another example, eye-monitoring system 104 may report eye-movement data based on previous eye-location data. Another example eye-monitoring system 104 may estimate future eye-locations based on eye-movement and current eye-location data. As still another example, eye-strength data may represent specific characteristics of the viewer-eyes (e.g., right eye, left eye, first viewer, second viewer, specific viewer identity, etc.)

In other embodiments, additional information about viewer-eyes may be determined by separate systems. For example, display system 100 might include eye-monitoring system 104, for determining eye strength, and a separate eye-tracking device for determining the viewer-eye's position.

III. Other Elements

As shown in FIG. 1, display system 100 may also include computing elements for control of system 100 and processing of signals to/from display screen 102, eye-monitoring system 104, and communication interfaces 116. In particular, display system 100 includes a processor 110 and a computer-readable medium (CRM) 112. CRM 112 may contain program instructions that processor 110 may execute to cause system 100 to perform certain functions. Processor 110 and CRM 112 may be integrally connected in a display device or these elements may connect locally or remotely to a display device.

Processor 110 may include any processor type capable of executing program instructions 114 in order to perform the functions described herein. For example, processor 110 may be any general-purpose processor, specialized processing unit, or device containing processing elements. In some cases, multiple processing units may be connected and utilized in combination to perform the various functions of processor 110.

CRM 112 may be any available media that can be accessed by processor 110 and any other processing elements in system 100. By way of example, CRM 112 may include RAM, ROM, EPROM, EEPROM, CD-ROM or other optical disk storage, magnetic disk storage or other magnetic storage devices, or any other medium that can be used to carry or store desired program code in the form of program instructions or data structures, and which can be executed by a processor. When information is transferred or provided over a network or another communications connection (either hardwired, wireless, or a combination of hardwired or wireless) to a machine, the machine properly views the connection as a CRM. Thus, any such connection to a computing device or processor is properly termed a CRM. Combinations of the above are also included within the scope of computer-readable media. Program instructions 114 may include, for example, instructions and data capable of causing a processing unit, a general-purpose computer, a special-purpose computer, special-purpose processing machines, or server systems to perform a certain function or group of functions.

In some embodiments, display screen 102, eye-monitoring system 104, communication interface 116, and/or other connected devices may include separate processing and storage elements for execution of particular functions associated with each system. As an example, eye-monitoring system 104 may store observed information (e.g., focal properties, gaze-tracking data, etc.) about viewer-eyes in an internal CRM and use internal processors to determine eye-strength. In this example, eye-monitoring system 104 may autonomously determine and transmit the eye-strength data instead of transmitting the observed information to central processor 110. Indeed, any of the processing, calculating, estimating, or control functions described above as being performed by display screen 102 or eye-monitoring system 104 may alternatively be performed by processor 110. In some cases, specific processors and CRM may be dedicated to the control or operation of one system although not integrated into that system. For example, processor 110 may include a display-control subsystem that uses a special-purpose processing unit to service display screen 102.

Display system 100 also includes communication interfaces 116 for communicating with local and remote systems. Communication interfaces 116 may include, for example, wireless chipsets, antennas, wired ports, signal converters, communication protocols, and other hardware and software for interfacing with external systems. For example, display system 100 may receive images for display via communication interfaces 116 from content providers (e.g., television, internet, video conferencing providers, etc.) or from local media sources (e.g., gaming systems, disc players, portable media players, computing systems, cameras, etc.) As another example, display system 100 may receive user-input and user-commands via communication interfaces 116 such as, for instance, remote control signals, touch-screen input, actuation of buttons/switches, voice input, and other user-interface elements.

IV. Illustrated Example Systems

Figure 3:
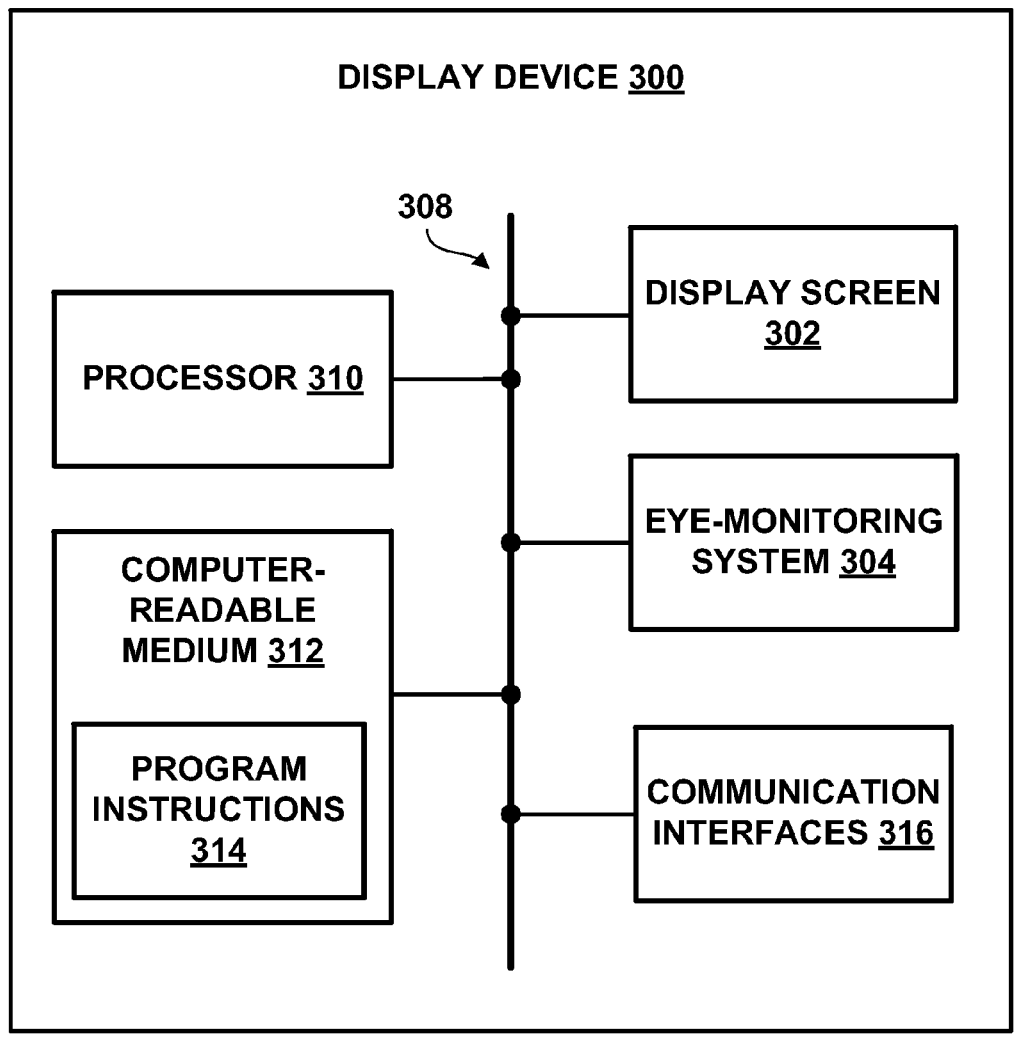
FIG. 3 is a schematic design of a 3D display device according to an exemplary embodiment.
Figure 4:
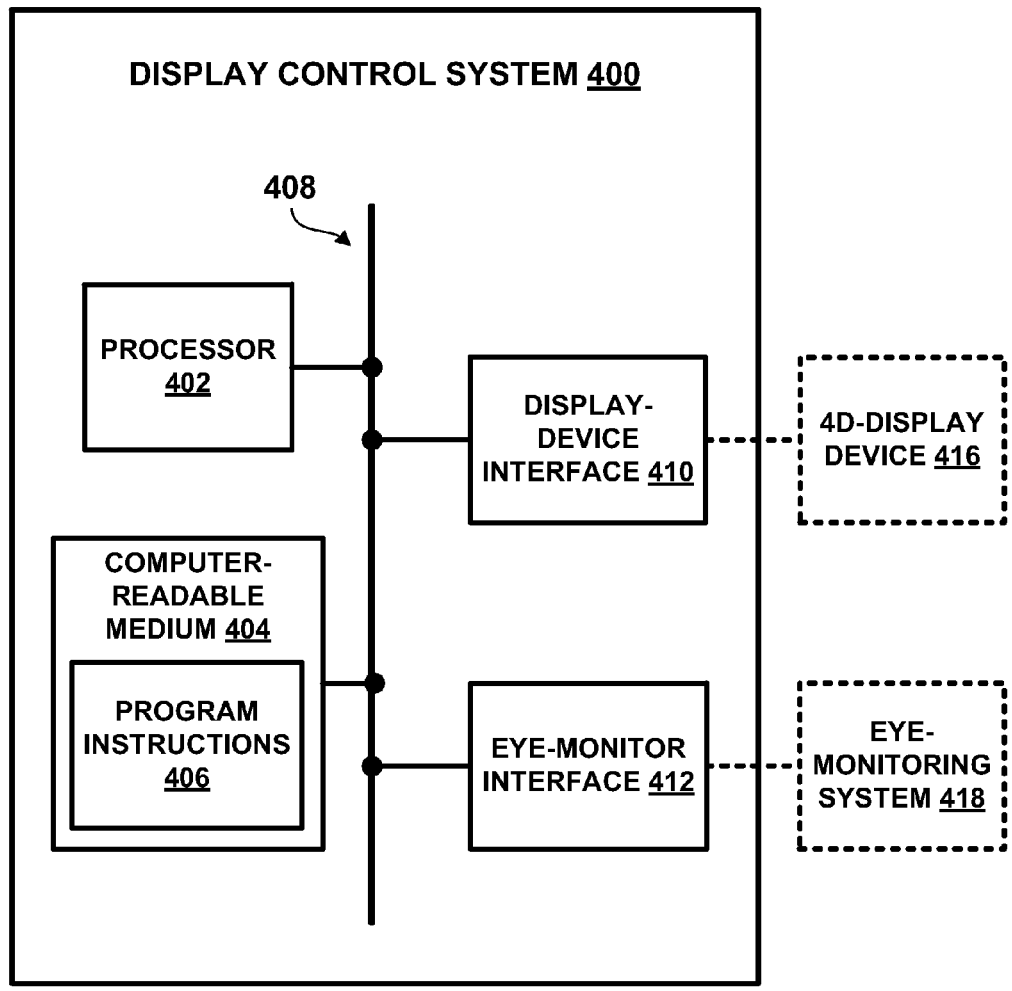
FIG. 4 is a schematic design of a display-control system according to an exemplary embodiment.
Figure 5:
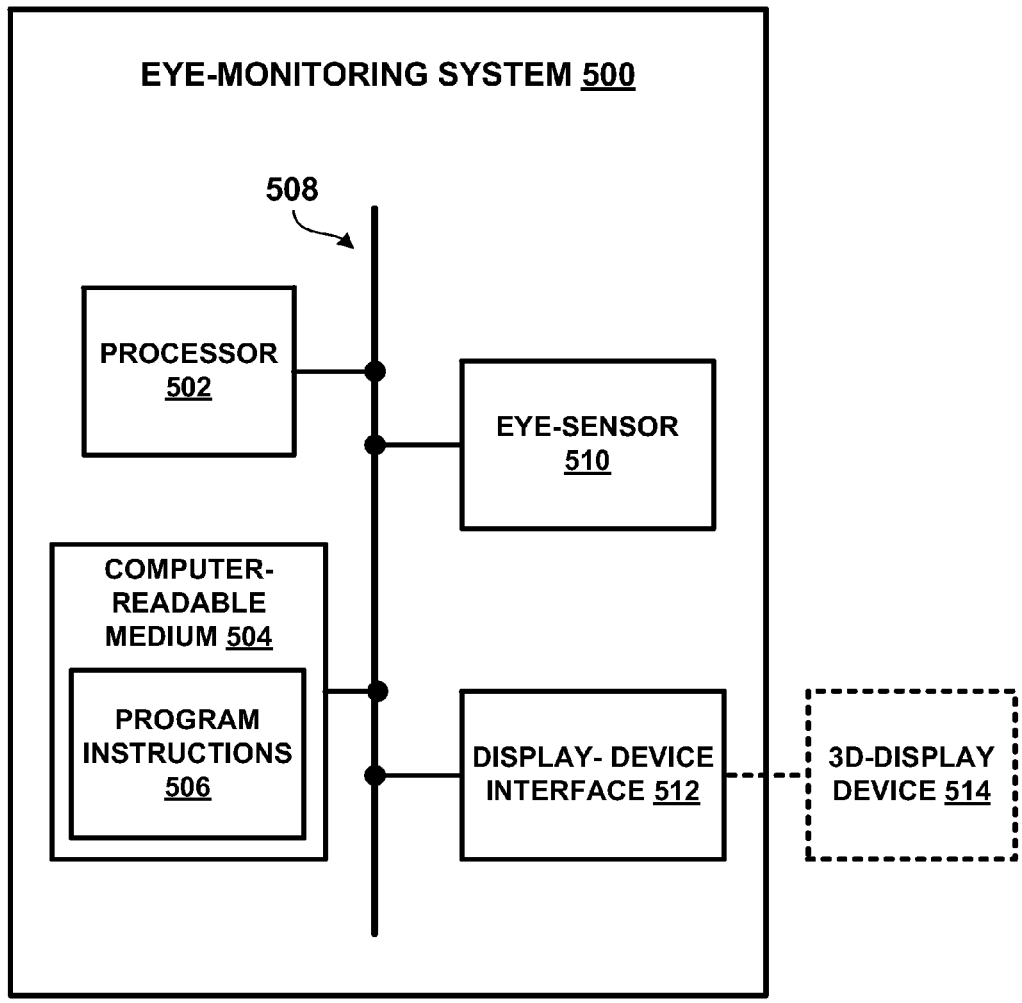
FIG. 5 is a schematic design of an eye-monitoring system according to an exemplary embodiment.

FIGS. 3-5 are schematic designs of particular device implementations according to exemplary embodiments. Elements shown in FIGS. 3-5 that are similar to elements described with respect to FIG. 1 (for example, processors 110, 310, 402, and 502) may be implemented and used in the ways described above with respect to FIG. 1. The devices and systems illustrated in FIGS. 3-5 are not intended to be exhaustive. Other arrangements and implementations will be clear to those of skill in the art, based on this disclosure.

FIG. 3 is a schematic design of a display device 300 according to an exemplary embodiment. As shown, display device 300 includes display screen 302, eye-monitoring system 304, processor 310, CRM 312, and communication interfaces 316, with each element communicatively coupled through system bus 308. Display device 300 may function as a self-contained unit, receiving content from communication interfaces 316 or CRM 312 and processing and displaying the content according to the functions set forth in program instructions 314 and data received from eye-monitoring system 304. Display device 300 may be any type of 3D display device or system containing the components shown in FIG. 3. For example, display device 300 may be a 3D-television system, a portable media player, a laptop computer, a desktop computer, a personal digital assistant (PDA), a mobile phone, or a self-contained gaming system, among other devices.

FIG. 4 is a schematic design of display-control system 400 arranged according to an exemplary embodiment. As shown, display-control system 400 includes processor 402 and CRM 404, which stores program instructions 406, communicatively coupled through system bus 408. Program instructions 406 may be executable by processor 402 to cause display-control system 400 to perform various functions as will be described. Some functions may involve communicating with 3D display device 416 and eye-monitoring system 418 through display-device interface 410 and eye-monitor interface 412. Interfaces 410 and 412 may include various hardware and software for communicating with 3D display device 416 and eye-monitoring system 418. Other exemplary display control systems may include additional components such as communication interfaces.

In some implementations, display-control system 400 may function as an external device to 3D display device 416 and eye-monitoring system 418. In other implementations, display-control system 400 may be integrated within a display system, display device, eye-monitoring system, or communication interface. In any arrangement, interfaces 410 and 412 may be simple electrical or optical connections, such as a pin connector or a fiber bundle; or complex interfacing systems, including chipsets, antennas, switching circuits, communication protocols, and/or dedicated program instructions, to name only a few examples.

FIG. 5 is a schematic design of an eye-monitoring system 500 arranged according to an exemplary embodiment. As shown, eye-monitoring system 500 includes processor 502, CRM 504, which stores program instructions 506, and eye sensor 510, all communicatively coupled through system bus 508. Program instructions 506 may be executable by processor 502 to cause eye-monitoring system 500 to perform various functions as will be described. Some functions may involve communicating with 3D display device 514 through display-device interface 512. Eye sensor 510 may include any of the various sensors, emitters, In some implementations, eye-monitoring system 500 may function as independent device externally connected to 3D display device 514. In other implementations, eye-monitoring system 500 may be integrated within a display system, display device, display-control system, or communication interface. Interface 512 may include various hardware and software, such as those described above with respect to interfaces 410 and 412. Other exemplary eye-monitoring system may include additional components such as communication interfaces, motion sensors, and displays.

Example Operation

Functions and procedures described in this section may be executed according to any of several embodiments. For example, procedures may be performed by specialized equipment that is designed to perform the particular functions. As another example, the functions may be performed by general-use equipment that executes commands related to the procedures. As still another example, each function may be performed by a different piece of equipment with one piece of equipment serving as control or with a separate control device. As a further example, procedures may be specified as program instructions on a computer-readable medium.

Figure 6:
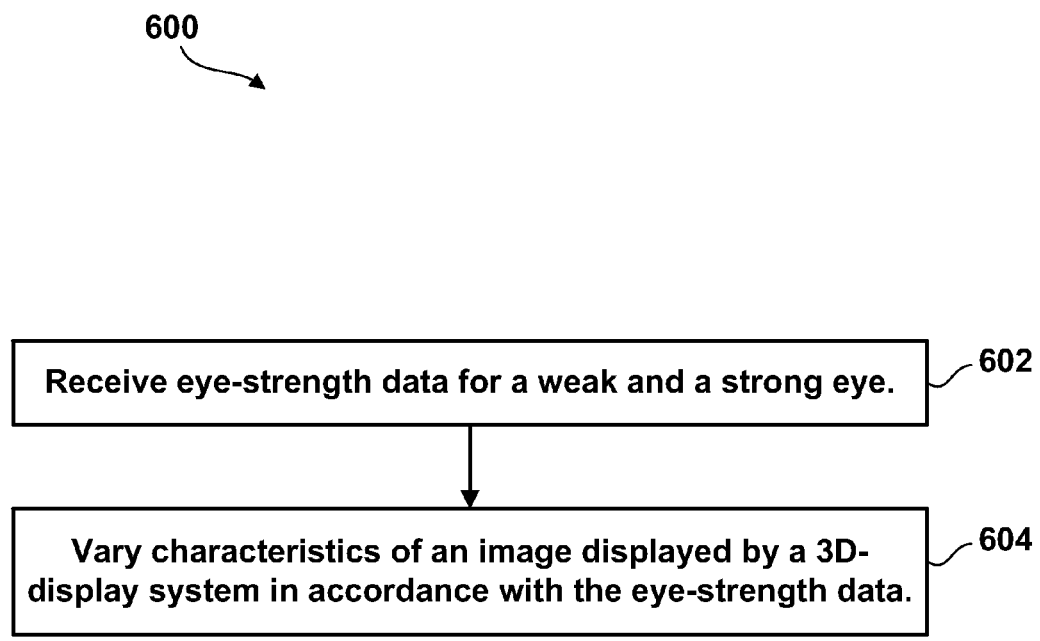
FIG. 6 is a flowchart of a process according to an exemplary embodiment.

FIG. 6 is a flowchart illustrating a method 600 according to an exemplary embodiment. As shown, method 600 involves receiving eye-strength data for a weak and a strong eye (step 602). Method 600 further involves varying characteristics of an image displayed by a 3D display system in accordance with the eye-strength data (step 604).

Figure 7:
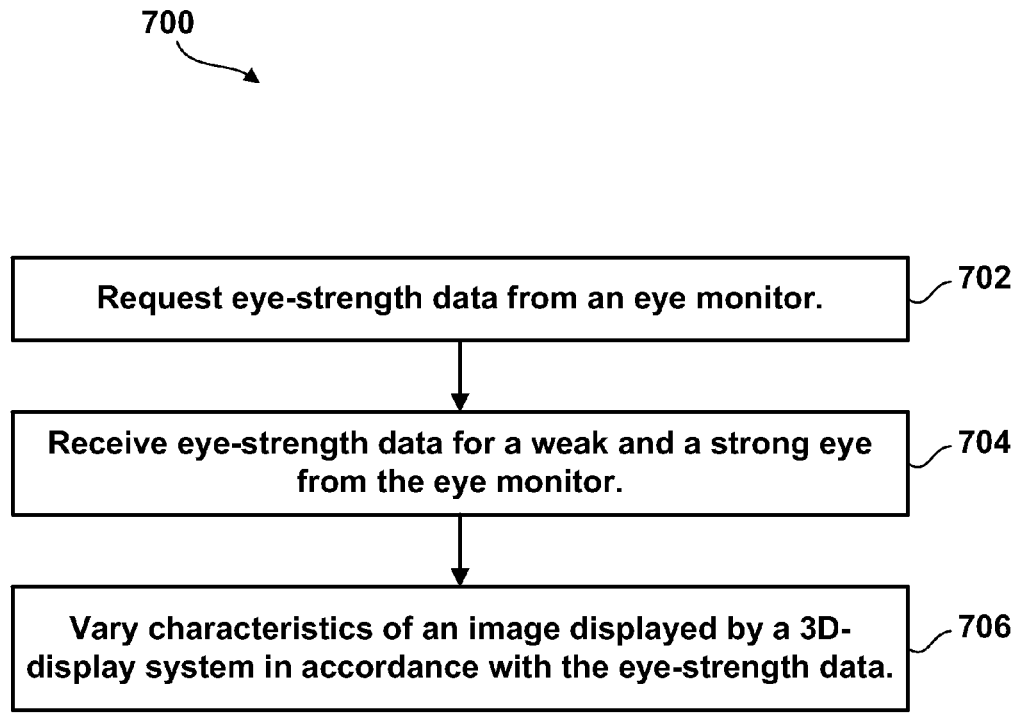
FIG. 7 is a flowchart of a process according to an exemplary embodiment.

FIG. 7 is a flowchart illustrating another method 700 according to an exemplary embodiment. As shown, method 700 involves requesting eye-strength data from an external eye monitor (step 702). Method 700 further involves receiving eye-strength data for a weak and a strong eye from the eye monitor (step 704). Method 700 further involves varying characteristics of an image displayed by a 3D display system in accordance with the received eye-strength data (step 706).

Figure 8:
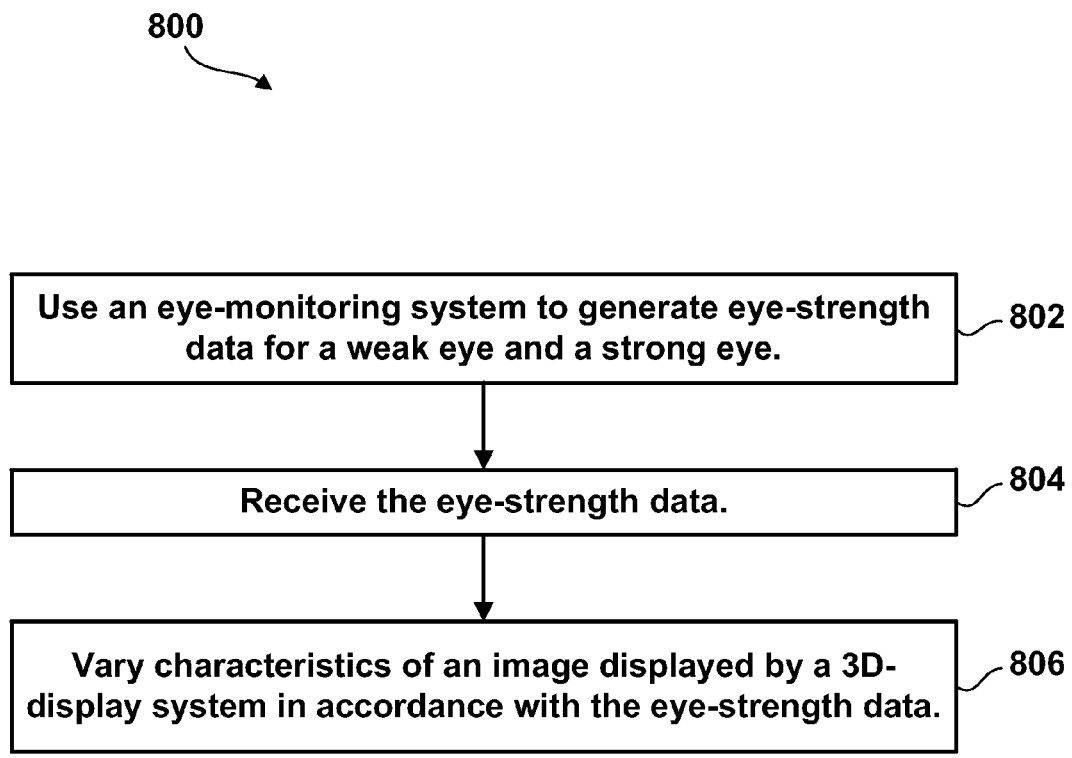
FIG. 8 is a flowchart of a process according to an exemplary embodiment.

FIG. 8 is a flowchart illustrating still another method 800 according to an exemplary embodiment. As shown, method 800 involves using an internal eye-monitoring system to generate eye-strength data for a weak and a strong eye (step 802). Method 800 further involves receiving the eye-strength data from the eye monitor to a processing unit (step 804). Method 800 further involves varying characteristics of an image displayed by a 3D display system in accordance with the received eye-strength data (step 806).

Figure 9:
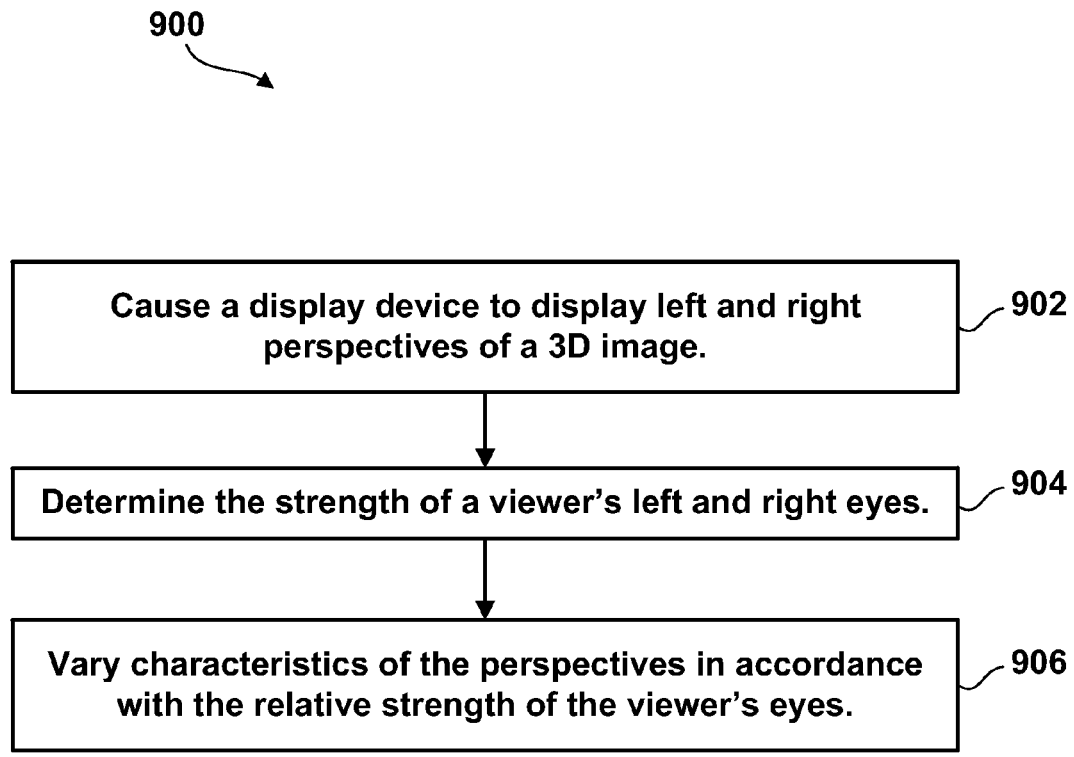
FIG. 9 is a flowchart of a process according to an exemplary embodiment.

FIG. 9 is a flowchart illustrating still another method 900 according to an exemplary embodiment. As shown, method 900 involves causing a display device to display left and right perspectives of an image (step 902). Method 900 further involves determining the strength of a viewer's left and right eyes (step 904). Method 900 further involves varying characteristics of the perspectives in accordance with the strength of the viewer's eyes (step 906).

Although FIGS. 6-9 show particular steps and particular step orderings, exemplary methods may include additional steps, omit shown steps, or reorder the steps in a variety of ways. In the following sections, aspects of each illustrated method, along with other exemplary procedures, are discussed with reference to the systems illustrated in FIGS. 1-5 and the example methods of FIGS. 6-9.

I. Requesting and Receiving Eye-Strength Data

A display-control system or display device may receive eye-strength data from various sources. For example, step 702 of method 700 involves requesting eye-strength data from an external eye-monitoring system. In other cases, eye-strength data may be received from integral eye-monitors into the processing components of a system. In still other cases, eye-strength data may be received as user-input as part of an eye-testing procedure or as determined by previous eye testing. In still other cases, stored eye-strength data may be loaded from CRM (such as CRM 112). In any case, the system may send a command, request, or instruction to initiate the generation of or access to eye-strength data.

For example, a system may periodically instruct an eye-monitoring system to generate eye-strength data. Such a system may periodically receive new eye-strength data while a certain viewer is watching the display. In this way, the system may track the progress or deterioration of the viewer's eye strength in real time. The system may adjust the amount of training or compensation that the viewer receives, in real time, in accordance with the tracked eye-strength.

As another example, eye-strength data may be requested whenever a new viewer is detected. A new viewer or a set of new viewers may be detected, for instance, when the display device is turned on. A system may also use sensors (such as the eye-monitoring system, an additional eye-detection system, or motion sensors) to determine that the viewership has changed. For instance, a display device may receive motion-sensor readings that indicate a threshold amount of movement in the device's viewing area and, in response to this detection, send a request to an eye-monitoring system.

In some cases, eye-strength data may be requested when the identity of the new viewer is recognized. For example, a viewer-profile may be stored in a display system or control device and activated by the viewer or an internal process whenever the viewer is watching the display device. The system may determine that the viewer is watching by using, for example, facial recognition, voice recognition, or user-input, among other examples. A viewer-profile may be stored on CRM 112 or on a local or remote storage system that communicates with system 100 through communication interfaces 116. A viewer-profile may include, for example, eye-strength data, results of previous testing or calibration, viewer preferences, data for use in recognition, historical data regarding previous viewing sessions, and/or other viewer information.

As a further example, a system may receive requests to generate eye-strength data from communication interfaces 116. In particular, a viewer (or a caregiver) may request that the system initiate eye-strength data gathering or generation via a user-interface. In another arrangement, a stand-alone eye-detection system may send a request via communication interfaces 116.

Any request for eye-strength data may include a variety of information pertaining to the requested data. For example, when a system requests eye-strength data associated with a particular viewer that the system recognizes, the request may include information about the particular viewer (e.g., name, system ID, data location of stored eye-strength data, previous eye-strength readings, etc.) As another example, the request may include information from other sensors that would be useful in monitoring the eyes (e.g., position of the viewer, positions of each eye, movement of the viewer, characteristics of currently displayed content, etc.) As a further example, the request may include instructions for collecting the data (e.g., number of times to test, a time period over which to repeatedly test, additional data to collect with eye-strength data, desired format of the eye-strength data, etc.)

The system may also receive eye-strength data without requesting the data from external or internal systems. In particular, eye-monitoring systems may be programmed to generate or collect eye-strength data at certain times (e.g., periodically or in response to certain stimuli) and send the data to a display or control system. In other cases, an eye-monitoring system may receive requests for data from external sources without the interaction of a display system or display control. In still other arrangements, remote servers or systems may send eye-strength data via communication interfaces 116 to a display system.

Whether received data is requested or unrequested, the system may process eye-strength data to determine the eye-strength of viewer-eyes. In particular, the system may compare eye-strength data for each eye to determine a relative eye-strength. In some cases, the display system may receive raw collected data from an eye-monitoring system and process the data to determine and/or compare the eye-strength that the data indicates. In other cases, as will be described, the display system may receive eye-strength data that an eye-monitoring system has already processed from raw collected data.

The relative eye-strength may be represented by Boolean variables (i.e., an eye is either "strong" or "weak"), a qualitative description (an eye is much stronger, much weaker, slightly weak, etc.), or a quantitative description (an eye's strength is reported as a numerical representation). In some cases, eye-strength data may only indicate the relative eye-strength of viewer-eyes (i.e., how a viewer's eyes compare to each other). In other cases, the eye-strength data may indicate the absolute eye-strength of the viewer's eyes (i.e., how each eye compares to a standard measure of eye strength).

In some cases, the eye-strength data may include eye-strength readings for each eye. In other cases, the eye-strength data may indicate only the difference in eye strength. In still other cases, the data may indicate the absolute eye-strength value for the weak viewer-eye, but not for the strong viewer-eye.

Some example display systems may receive eye-strength data from external sources via communication interfaces 116, instead of receiving eye-strength data from an eye-monitoring system. For example, if a viewer already received an eye-strength test, such as a professionally administered test, then the results of that test may be entered into a display system through communication interfaces 116. As another example, a system may request and receive eye-strength data from an external database or server. In addition to the value of eye strength, such data may indicate other pertinent information with regard to the viewer's vision. For example, the data may include information regarding such vision problems as cataracts, color blindness, and near-/far-sightedness. Other examples are also possible.

II. Generating Eye-Strength Data

Eye-monitoring system 104 may use a variety of eye-characteristics to determine the eye strength of a viewer-eye. For example, eye-monitoring system 104 may track the gaze direction of each viewer-eye to determine whether there is a difference in how much each eye moves. If the viewer moves one of his or her eyes less than the viewer moves the other, this may indicate that the less mobile eye may be weaker than the more responsive eye. In some embodiments, a control system may locate the focal point of an image that is displayed on display screen 102 and use this determined focal point in combination with the gaze-tracking data to determine eye strength. For example, while display screen 102 is displaying a video in which an emphasized object moves across the image in one direction, eye-monitoring system 104 may track the gaze-direction of viewer-eyes to determine how much each viewer-eye moves in that direction. Then, a control system may correlate the movement of the emphasized object and the eyes to determine whether one eye is weaker (e.g., less used or less responsive) than the other.

For a viewer with a strabismus (a condition in which the eyes are not properly aligned to each other), the system may use gaze-tracking information to determine how often the viewer fixates with each eye. If the viewer has equal eye-strength in each eye, the viewer will alternate between fixating with the right eye and fixating with the left. The fixation may be observed as a turning of the eye to face the object of interest (in this case, the display screen). When a viewer with strabismus switches the eye with which they are fixating, the viewer's eyes move slightly to the left or right. A system may track these movements and record the amount of time spent fixating with each eye. The difference in the time spent fixating with each eye may then be used as a measure of eye strength.

As another example, eye-monitoring system 104 may use dilation data to determine the eye-strength of viewer-eyes. In particular, a weak viewer-eye may respond to changes in light slower than a strong viewer-eye. Hence, eye-monitoring system 104 may detect eye strength by determining the difference in dilation characteristics of each eye. A system may also analyze the brightness of images presented to the viewer for comparison to detected dilation changes. For example, when the system detects that a displayed image has significantly increased in brightness, the system may track corresponding dilation changes with the expectation that responsive eyes will dilate less to adjust for the increasing brightness.

As a further example, eye-monitoring system 104 may detect the focus of the viewer-eyes and use the detected focus as an indication of eye-strength. The focus of a viewer-eye in this sense is a measure of the depth of the viewer's gaze. An eye sensor may detect focus, for example, by emitting light through the center of the eye, so that the light reflects off the back of the eye, and analyzing the reflected light to determine characteristics of the eye's lens. Processors in eye-monitoring system 104 or connected to display system 100 may then compare the depth of focus for each eye with respect to the other eye and with respect to the viewer's distance from display screen 102. A difference in focus may indicate a difference in eye strength between the viewer-eyes. For example, a weak eye may focus on a depth that is significantly different from the physical distance from the viewer to display screen 102, because the viewer is not relying on that eye for looking at the screen. In other implementations, a gaze-tracker may facilitate determining the viewer's focus-depth by comparing the two eyes' directions. For example, the level to which a viewer crosses or uncrosses his or her eyes may indicate the viewer's focus depth. In such an arrangement, the system may then compare the focus indicated by the eye-directions to the focus of the individual eyes as determined by reflecting light off the back of the eyes.

Some embodiments may generate eye-strength data without actively monitoring a viewer's eyes. Instead, such embodiments may receive data from communication interfaces 116 and process this data to generate eye-strength data. For example, a system may conduct an eye-strength test by presenting images to a viewer, receiving viewer-input, and correlating the viewer-input to the presented images to determine eye strength. In particular, a system may show a succession of images in which the brightness of the image reduces until the viewer indicates that the image is no longer visible. As another implementation, a system may display 3D images in which one of the perspectives is reduced in brightness and ask the viewer to indicate "good" images and "bad" images. In a further implementation, a viewer may perform a side-by-side comparison in which (1) an image is displayed to each eye so that the two images are beside each other, (2) the viewer varies the display brightness of one or both images, and (3) once the images appear equivalent, the viewer indicates that the current altered brightness settings produce equivalent perspectives. Based on the viewer-input, the system may determine the relative or absolute eye-strength of the viewer and generate corresponding eye-strength data. Although brightness is used as an example of an altered characteristic in the above examples, any of the described embodiments may involve varying other display characteristics instead of, or in addition to brightness.

In a gaming system with a 3D display, the eye strength of a viewer (player) may be determined by altering image characteristics while the viewer is playing a game and monitoring how well the viewer plays. For example, a display system may receive updates from the gaming system indicating how well the player is performing in a 3D-graphics-based game. Then, in response to detecting that the viewer plays worse when a first perspective is dimmed, the system may report that the viewer-eye associated with the first perspective is the weak viewer-eye. Correspondingly, in response to detecting that the viewer plays better when the first perspective is dimmed, the system may report that the viewer-eye associated with the first perspective is a strong viewer-eye. If, instead, a 2D-graphics-based game (or 3D game that does not require much 3D) is used, then dimming the perspective displayed to the dominant eye may actually decrease the player's effectiveness, reversing the resulting diagnosis.

In some embodiments, eye-strength data may also indicate information about the detected viewer-eyes other than just the eye-strength. For example, eye-monitoring system 104 may be configured to detect the locations and/or motion of the viewers' eyes and include this detected information in the eye-strength data. As another example, when the system detects two viewer-eyes that move together and/or are separated by less than a certain distance, eye-monitoring system 104 may determine that the viewer-eyes belong to a single viewer and indicate the left viewer-eye and the right viewer-eye in the eye-strength data.

Some example systems may be configured to serve multiple viewers at once. In particular, a system may detect multiple eyes in the viewing area and determine which of the viewer-eyes most likely belong to the same viewer. The system may use one of a variety of techniques to determine the likelihood that particular eyes belong to the same viewer. For example, the system may use the location and motion of each of the viewer-eyes and determine whether the separation or relative movement of the eyes is indicative of the viewer-eyes belonging to a single viewer. As another example, a camera-based eye-monitoring system may determine whether viewer-eyes belong to the same viewer by comparing images associated with each viewer-eye to detect assess the similarity between the eyes. In response to determining that the viewer-eyes are threshold similar, the system may determine that they belong to the same viewer. In some cases, a system may annotate data that represents a viewer's pair of eyes with an identifier of the particular viewer represented by the pair of viewer-eyes. For example, in response to determining that two pairs of eyes belong to two viewers, a system may label each pair as "VIEWER A" or "VIEWER B." Other labels may also be used and viewer-eye data may include many other forms of information as well.

In a system where eye-monitoring system 104 detects the location of viewer-eyes, the eye-strength data may indicate the relative directions (i.e., a relative angular position vector) from display-screen 102 to the detected eyes. Such directional position data may be gathered, for example, by comparing the direction from eye-monitoring system 104 towards the detected eyes to the position/orientation of eye-monitoring system 104 relative to the display screen. Additionally, eye-strength data may indicate the relative distance from the display screen to the detected eyes. For example, a proximity sensor may determine relative distance of a detected object by outputting light or sound waves, detecting returning waves, calculating the propagation time of the waves, and using the speed of propagation to calculate the distance of the object off which the wave reflected.

Eye-strength data may also indicate the movement of detected eyes. For example, eye-monitoring system 104 may determine eye-locations occasionally and compare the determined set of eye-locations with one or more previous eye-locations in order to estimate the motion of detected eyes. In determining motion of a particular eye, the eye-location data from a current set of eye-locations may be associated with corresponding eye-location data in each of several previous sets of eye locations. For example, the eye locations may be associated based on a detected similarity in the data that represents each corresponding eye-location (e.g., image, geometry, reflectivity or other similarities of the data). As another example, corresponding eye-locations may be associated based on a detected similarity in their position relative to other eye-locations.

Using the current and previous values of eye-location from the associated eye-location data, eye-monitoring system 104 may calculate motion characteristics associated with the determined eye-locations. Such motion information may include, for instance, speed, direction of movement, velocity, acceleration, movement pattern, and/or jerk, among other movement characteristics. Eye-monitoring system 104 may then include the determined motion information in the eye-location data that it sends to the control, processing, or other elements of display system 100.

In some cases, eye-monitoring system 104 may process motion information and current eye-location data in order to estimate future eye-locations. For example, in response to determining that a detected eye is moving in a particular direction at a particular speed, eye-monitoring system 104 may estimate the distance the eye will move in a given duration of time by multiplying the given duration by the particular speed. Eye-monitoring system 104 may then estimate the eye's future location at the end of the given duration by adding the estimated distance in the particular direction to the current eye-location. In other arrangements, the system may factor acceleration, jerk, or the other motion information into an estimation of the future eye-location. Then, eye-monitoring system 104 may include the future eye-location data in the eye-location data that it sends to control elements in system 100.

In some embodiments, an eye-monitoring system (or other system that generates eye-strength data) may send raw collected data to a display system. For example, eye-position, movement, focus, alignment, and/or dilation data may simply be collected and transmitted to display-system processors. In such a case, the display-system processors may perform the techniques described above to determine and/or compare eye strength. In other embodiments, the eye-monitoring system may process the data to determine or compare eye strength and send the resulting data to the display system. In still other embodiments, an eye-monitoring system, such as system 500, may fully process the eye-strength data and autonomously determine adjustments to be made to the displayed images. In such an embodiment, the eye-monitoring system may send eye-strength data to the display system or device in the form of instructions, directing the display system how to adjust for the eye-strength. Such instructions may be indicative of the eye-strength, therefore, without explicitly indicating the eye strength.

III. Varying Display Characteristics

At step 604, method 600 of FIG. 6 involves varying the display characteristics of an image displayed by a 3D display system in accordance with the received eye-strength data. Similar procedures are performed at steps 706, 806, and 906 of methods 700, 800, and 900 respectively. In some cases, a single display device or system may determine how to vary display characteristics and vary the characteristics. In other cases, a control system, such as display control system 400, may determine how to vary the display characteristics and cause a separate display device to vary the characteristics. As will be described, a system may vary any of various display characteristics such as, brightness, resolution, complexity, image size/position, peripheral content, spectral content, saturation, or temporal complexity, among other examples.

As stated earlier, a 3D display system may be used to display 3D or non-3D images. The images that are displayed to each eye are referred to as perspectives in the following sections regardless of whether the images combine to give the impression of depth (e.g., 3D images) or not (e.g., non-3D images).

In some embodiments, a system may vary the brightness of a displayed perspective. In one implementation, a system may vary the brightness by changing the luminance of each pixel associated with the perspective. For example, a system may determine which pixels are associated with the perspective and vary the amount of electrical current delivered to a light source to alter the luminance of the source. As another example, a system may use optical filters to reduce the brightness of a perspective by absorbing light from pixels associate with the perspective. In another implementation, a system may vary the brightness by changing the amount of time that each pixel associated with the view is emitting light. Such an implementation may function through active pulsing of the light or through pulsed wave modulation (PWM) technique. In a further implementation, a system that displays two perspectives from the same pixels (e.g., by sequentially displaying each perspective) may vary brightness by changing the amount of time the pixels display each perspective. In yet another implementation, a system may turn off a portion of the pixels associated with one perspective.

Figure 10A:
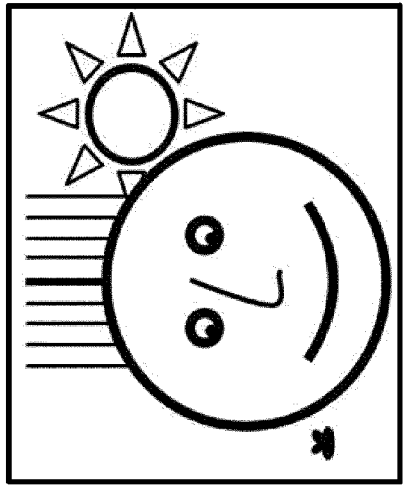
FIGS. 10A-10F illustrate example variations that may be made to display characteristics of an image.
Figure 10B:
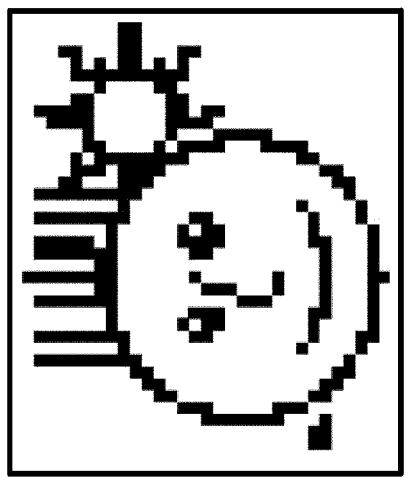

In some embodiments, a system may vary the spatial resolution of an image. The spatial resolution of a displayed image refers to the number of independently addressable pixels the display uses to produce the image. In order to reduce the spatial resolution of an image, a set of adjacent pixels may be assigned a single address so that the pixels in the set of adjacent pixels all display the same portion of the image. Such a modification is illustrated by FIGS. 10A and 10B. FIG. 10A shows an unmodified image that could be a perspective of a 3D image. FIG. 10B shows the same image with a reduced spatial resolution. To reduce the spatial resolution, a system may detect what color would be displayed in full resolution image by each pixel in the set, determine an average color for the set, and display that color for every pixel in the set. In the example of FIG. 10B, a set of nine pixels are averaged into a single pixel by counting the number of white pixels and black pixels in the set and choosing either white or black depending on which color is more prevalent. This type of average color may be called the "mode" of the pixels. In other examples, the system may use a lighter or darker shade of gray for the average color depending on whether the percentage of black pixels is lower or higher, respectively. This average color is closer to a "mean" average color.

In color images, the system may also reduce the spatial resolution of the image by choosing an average color. The average color may be chosen as the most prevalent color (the mode) or as an intermediate color (the median or mean). Choosing an intermediate color may be more complicated in a color image than in a black/white or grayscale image. In choosing such a color, the system may rank all the colors used in the set of pixels based on one or more characteristics of the color (e.g., hue, brightness, saturation, amount of red in an RGB system, amount of cyan in a CMYK system, etc.) Then, to choose a "median" color, the system may find a color that is in the middle of the rankings and select this color as the average color. Alternatively, the system may choose a mean color by (1) assigning each color a numerical value, based on the ranking criteria; (2) calculating the numerical mean of the assigned values, and (3) picking the color that would be associated with that numerical value. For example, if ranking is based on hue, then the system may use a standard set of hue variants (such as the 256-hue system used in many computing applications) to assign a value to each color from a group of pixels, calculate the mean value, and use the same standard system to pick the color associated with the mean value. Hence, the mean color may be a color that would not be displayed in any of the pixels from the full-resolution image, but rather, represents the average value of the full-resolution colors. Because many color systems use multiple independent variables (e.g., RGB, CMYK, and HSL variables, among others) to define a color, the determination of a mean or median color may take a separate calculation for each variable. Although the example of FIG. 10B shows sets of nine pixels that form squares being averaged, an example system may reduce the spatial resolution by averaging any number of pixels that form any of several shapes.

In some embodiments, a system may vary the complexity of a displayed perspective. For example, a system may remove features of one perspective to make the perspective less complex. A feature may be removed, for instance, by turning off pixels related to that feature. In other embodiments, a feature may be removed by changing the color the pixels to the color of the pixels surrounding the feature. For example, to remove a black line across a green background, a display may change the pixels in the line from black to green. In grayscale or color images, a system may use image-processing techniques to define what a "feature" of the image is and what portion of the image it occupies.

Figure 10C:
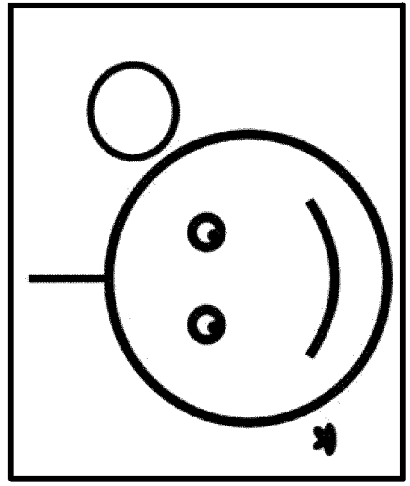

To determine which features to remove, the system may use several techniques, some of which are shown in FIGS. 10C-10F. As illustrated in FIG. 10C, a system may determine the size of the various features within an image and reduce complexity by removing features below a certain size from one perspective. In the example FIG. 10C, lines are removed based on their thickness. Other examples of feature size may also be used as criteria for distinguishing between large and small features such as, length, pixel area, 3D volume (the product of the area across the screen and the perceived depth of a 3D feature), 3D surface area (the topographical surface area of a feature calculated from two of: length, width, and perceived depth).

Figure 10D:
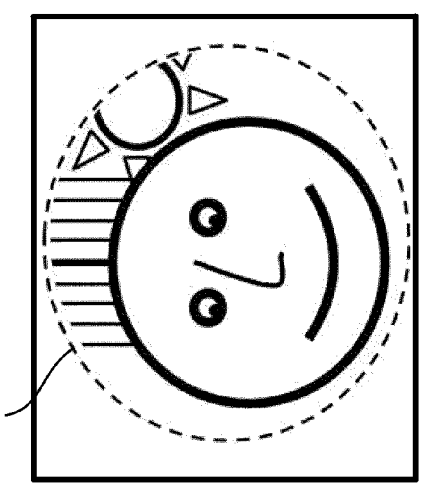
Figure 10E:
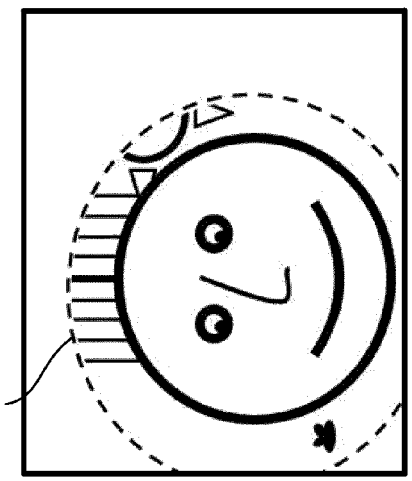

As shown in FIGS. 10D and 10E, a system may reduce complexity by removing features at the periphery of an image (also known as "peripheral content"). For example, a system may remove features near the edge of the screen. Such an example is shown in FIG. 10D, in which the system defines a border 1002 around the center of the image As another example, a system may receive indications of which portion of an image is the focal point or center of attention and remove features that are far from this focal point. FIG. 10E shows an example of a system that defines a border 1004 around a focal point of the image. Although borders 1002 and 1004 are shown as oval-shaped and slightly smaller than the full screen, a system may use any shape or size of boundary to distinguish between peripheral content and the rest of the image. Because the peripheral content is removed outside of the border, the size, shape, and position of the border may, in this case, define an "image size," an "image shape," and an "image position." In some cases, the removed "peripheral content" may actually be at the center of the image or center of attention in the image. For example, a system may remove important features (e.g., features that are indicated as focal points of an image) from the perspective of the strong viewer-eye, so that the viewer must rely more heavily on the weak eye. Such a variation may be particularly effective in a 3D-gaming application, because the viewer may need to see particular 3D-features in an image to succeed at the game.

Figure 10F:
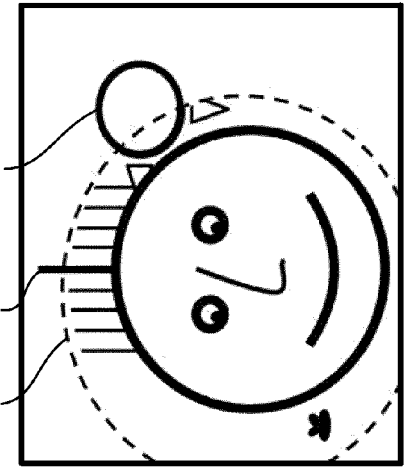

As shown in FIG. 10F, a system may also combine complexity-reducing techniques. In particular, the image of 10F illustrates a technique in which a border 1006 defines the periphery of the image and small features in the periphery are removed. Larger features in the periphery, such as line 1008 and arc 1010 have not been removed by this technique. In other embodiments, the spatial resolution, spectral content, or other characteristic of peripheral content may be varied. More generally, a system may define image portions of any number, size, and shape in which to vary any of the display characteristics. For example, a system may increase the brightness of one side of the image. As another example, a system may reduce the temporal resolution of most of an image, while continuing to display a particular feature in an image at a non-reduced temporal resolution. Other examples are also possible.

In some embodiments, a system may vary the spectral content of a perspective. For example, a system may reduce the spectral content of a perspective by filtering the perspective to reduce the number of different colors that are displayed in the perspective. In particular, such filtering may involve comparing each pixel in the full-color image to a reduced set of colors and selecting the color from the reduced set that most closely resembles the original color of the pixel. In some cases, the reduced set of colors may include a relatively full range of colors (such as a standard 16 or 256 color set). In other cases, the reduced set of colors may include only colors from a particular color palette. For example, a system may include only colors with a reduced saturation (i.e., colors that are spectrally broadened to produce a "grayed out" image) in a reduced set of colors.

In other embodiments, a system may vary the color saturation of a perspective by applying a uniform filter to all pixels in the perspective. For example, a system may increase the color saturation by altering the frequency spectrum of the light that each pixel emits so that each pixel emits only a single frequency of light. In practice, a saturated color may contain some light that is outside of the single desired frequency, but the spectrum overall would have a single narrow peak in intensity at the desired frequency and reduced intensity at frequencies outside of the peak. As another example, a system may reduce the saturation by reducing the intensity of light that is emitted at the peak frequency or by increasing the intensity of other frequencies. In some embodiments, the intensity of light at the peak frequency of each pixel may be entirely equalized to the intensity of light at non-peak frequencies of that pixel, producing a grayscale image.

In some embodiments, a system may vary the temporal resolution of a perspective of a 3D video. For example, the system may reduce the rate at which frames change for one perspective. In particular, the system may reduce the frame rate in half by displaying each frame for twice the normal duration. To maintain consistency between the perspectives, the system may refrain from displaying every other frame of the reduced perspective of the 3D video. In this way, the two perspectives may present a coherent image, but one perspective with also display an intermediate image. A system may reduce the frame rate to rates other than simply half the normal rate. For example, the same strategy could easily be applied to frame rates that are one-third, one-fourth, or one-fifth as frequent. Further, frame rates of any arbitrary ratio may be simply accomplished by refraining from displaying the appropriate portion of frames. In some embodiments, the system may also change when the frames of the reduced perspective are refreshed, so that the reduced frame rate is regular. For example, if the reduced frame rate is two-thirds of the normal frame rate, then, instead of refreshing the image simultaneously with the normal perspective for two frames and not refreshing at the third frame, a system may delay the refresh time of the second frame by a half duration. In this way, the system refreshes the reduced perspective regularly, at durations that are 1.5 times longer than the normal duration.

Example systems may also vary multiple display characteristics in combination. For example, a system that increases the saturation of a perspective may also increase the brightness of the perspective. As another example, a system may reduce both the spatial resolution and the temporal resolution of one perspective. Other examples are also possible.

In addition to controlling whether any of the above-described display characteristics are changed, a system may also control how much a characteristic is changed. For example, a system may brighten a pixel a small amount by slightly increasing the electrical current through the light source, and brighten the pixel a large amount by greatly increasing the electrical current through the light source. As another example, a system may define a larger or smaller area of the image to be "peripheral content" that is subject to reductions in complexity or resolution. Similar control can be applied to resolution, spectral content, temporal resolution, saturation, and other display characteristics.

In order to determine how much to vary the display characteristics, the system may evaluate the difference in eye strength between a viewer's eyes. In some cases, a system may refrain from varying the display characteristics in response to determining that the difference in eye-strength is smaller than a predefined threshold difference. In such a case, the system may evaluate the difference in eye-strength by comparing the difference to the preset threshold level.

Some systems may use multiple threshold values to determine which characteristics to vary and how much each characteristic should be varied. For example, the system may vary the spatial resolution of a perspective in response to determining that a detected eye-strength difference is larger than one threshold value and vary the complexity of the perspective in response to the difference being larger than a different threshold value. As another example, in response to detecting a difference that surpasses a low threshold value, a system may reduce the temporal resolution of a perspective by one-half and, in response to detecting that the difference is larger than a higher threshold, the system may reduce the temporal resolution by one-third.

Some systems may use a sufficient number of threshold values that correspond to amounts of display varying that the range of values are substantially continuous. In particular, a system may assign a numerical scale to the amount that a display characteristic may be varied and, then, vary that characteristic in direct proportion to the eye-strength indicated in the eye-strength data. For example, the system may assign a numerical scale to the possible values of brightness for an image and then fit possible differences in eye strength to the same numerical scale. When such a system receives eye-strength data, the system may use these assigned values to match the difference in eye-strength indicated in the received eye-strength data to the amount of varied brightness. A system may also assign values to more than one display characteristic, so that multiple characteristics may be varied in proportion to the eye-strength difference. In such an embodiment, the particular display characteristics may either be varied over the entire range of eye-strength differences or be varied only in certain ranges. For example, a system may vary one characteristic when the eye-strength difference is small and vary a different characteristic when the eye-strength difference is larger.

In a system that occasionally (e.g., periodically) receives or generates new eye-strength data, the system may also occasionally update whether, and how much, particular display characteristics are varied. For example, each time that new eye-strength data is received, the system may determine how the viewer's eye strength has changed and adjust the display characteristics accordingly. In some embodiments, instead of adjusting display characteristics in direct response to each reception of new eye-strength data, the system may analyze (e.g., using filtration, curve-fitting, linear or nonlinear regression, etc.) a set of eye-strength data to identify a time-dependent trend. The system may then adjust display characteristics in accordance with the trend. In this way, some embodiments may cause a predictive adjustment, based on a forward projection of the trend.

IV. Compensating for a Weak Viewer-Eye

In varying the display characteristics, some variations may make the perspective more or less complex. For example, decreasing the image complexity, image size, amount of peripheral content, spectral content, spatial resolution, and/or temporal resolution of a perspective may decrease the complexity of the perspective, because the eye has less visual information to receive and process.

Other variations may make the perspective easier or harder to view or recognize. Such a variation may be herein termed a change in viewing difficulty. For example, increasing the brightness, saturation, or contrast of a perspective may decrease the viewing difficulty, because the visual information may be easier to see and/or discern. In contrast, decreasing the brightness, saturation, or contrast of an image may increase the viewing difficulty. Some changes to viewing difficulty may be less direct. For example, if image-complexity variations are taken to the extreme, like the resolution change shown in FIG. 10B, then the viewing difficulty may actually increase, because the image will be harder to discern. That is, the natural ability of the mind to group bits of information into larger objects may be degraded, causing the viewer to use conscious energy to analyze the image. As another example, moving the image position (by changing the position of removed peripheral content) to an area that is not near the original image center or center of attention may increase the viewing difficulty, because removing the focal point may make the image less recognizable.

In practice, a system may vary image complexity and viewing difficulty of a perspective relatively: that is, with respect to the other perspective. Because relative changes to one perspective may be thought of as producing opposite changes to the other perspective, the system may relatively vary the characteristics of one perspective without actually changing that perspective. For example, decreasing the spatial resolution of the perspective associated with the strong viewer-eye may be taken as an increase to the spatial resolution of the perspective associated with the weak viewer-eye. In other cases, the system may actually vary the display characteristics of the intended perspective (which amounts to an absolute change and a relative change). In some cases, the system may determine how to vary the display characteristics based on whether a change is even possible. For example, if an original image is already at the full spatial resolution of the display device, then the system may increase the spatial resolution of a perspective only by decreasing the resolution of the other perspective.

When a system detects a weak viewer-eye, the system may compensate by decreasing the viewing difficulty of the perspective presented to the weak eye and/or decreasing the image complexity of the same perspective. Because a viewer may perceive or distinguish less visual-information through the weak eye than the strong eye, a decrease in viewing difficulty may give the viewer the impression that each of his or her eyes are receiving images equivalently. For example, if eye-strength data indicates that the weak viewer-eye has dimmed eyesight (i.e., less of the light received by the eye is perceived by the brain than on a normal eye), then a system may increase the brightness of the image to this eye (or a decrease the brightness of the view to the other eye) so that the viewer perceives the same amount of light through each eye.

A system may reduce the image complexity, for example, to conserve resources without reducing the quality of the displayed 3D image. For example, if the eye-strength data indicates that the weak viewer-eye is blurry (i.e., having a lower spatial resolution than a normal eye), then a system may reduce the spatial resolution of the perspective to this eye without the viewer perceiving the change. As another example, if the eye-strength data indicates that a viewer has a cataract at the top of the weak eye, then a system may increase the brightness of the top of the perspective associated with this eye. As a further example, if the eye-strength data indicates that the weak viewer-eye is wholly or partly color blind, the system may reduce the saturation or spectral content without greatly affecting the viewer's perception. In the example of one color-deficient eye, the system may also reduce the saturation or spectral content of the perspective associated with the dominant viewer-eye, to conserve resources associated with display of a saturated color image and to avoid the situation where the colors of the two perspectives disagree.

In compensating for the weak viewer-eye, a system may limit the amount to which the complexity or viewing difficulty is reduced, so that these variations do not further weaken the viewer-eye. In particular, when the complexity or resolution of the weak viewer-eye's perspective is reduced, the viewer may rely less on that perspective and, instead, rely more on the dominant eye. Such reliance may further exacerbate the eye's weakness by obviating the use of the weak viewer-eye. To help avoid this issue, the system may use eye-strength data and/or eye-location data to estimate the amount of image change that would be indiscernible by the viewer. Then, the system may use this estimated amount of change as a cutoff and not allow the display characteristics to vary more than the cutoff. In practice, a system may maintain changes well below the cutoff in case of incorrect estimation. As an example of estimating, a system may determine (or receive already determined) the maximum resolution that a weak viewer-eye can discern at a given distance and scale that resolution to the distance between the display screen and the detected eye-locations.

V. Training a Weak Viewer-Eye

In addition to compensating for a weak viewer-eye, a system may be configured to train the weak viewer-eye so that the viewer may learn to rely more on the weak eye. To compensate for the weak viewer-eye, the system may decrease the viewing difficulty and/or complexity of the perspective associated with the weak eye. In contrast, to train the weak viewer-eye, a system may increase the viewing difficulty of the perspective associated with the strong viewer-eye and/or decrease the image complexity of the perspective associated with the strong viewer-eye.

The system may increase the viewing difficulty of the strong-eye's perspective to give the viewer the impression that each of his or her eyes are receiving images equivalently, in the same way that the system may decrease the weak viewer-eye's difficulty to give this impression when compensating for the weak viewer-eye. In contrast to the compensation technique, however, the system may increase the viewing difficulty for the strong eye beyond the level that gives a viewer the impression of equivalent perspectives. In some cases, the system may even completely turn off the strong viewer-eye's perspective so that the viewer must rely entirely on the weak eye. In other cases, the system may increase the viewing difficulty of the perspective of the strong viewer-eye until that perspective is only slightly less difficult to view than the perspective of the weak viewer-eye. In this situation, the viewer may compensate for the slight difference in viewing difficulty by relying slightly more on the weak eye. The viewer may not notice such a small increase in viewing difficulty and therefore the training is not intrusive.

Decreasing the image complexity of the strong viewer-eye's perspective may also cause the viewer to rely more on the weak eye without conscious effort. For example, a system may remove peripheral content from the strong-eye's perspective so that, in order to see the peripheral content, the viewer must rely on the weak eye. Because the content is not at the focus of the image, the viewer again may not notice the change but subconsciously may begin using the weak eye more. As another example, a system may reduce the temporal resolution of the strong viewer-eye's perspective so that the weak viewer-eye may receive more visual information in a given timeframe, without consciously performing an active treatment. In some cases, the system may both increase the viewing difficulty and decrease the complexity simultaneously. For example, a system may greatly reduce the spatial resolution of the strong eye's perspective so that the image is both more difficult to recognize and contains less visual information. As a further example, a system may remove important features from the strong eye's perspective as another technique for increasing viewing difficulty and decreasing complexity in the strong eye's perspective.

In some embodiments, the system may change over time how the display characteristics are varied. In some cases, a system may update how characteristics are varied when the system receives or generates new eye-strength data. In other cases, a system may initially vary the display characteristics in one way and, then, gradually change the amount of variation that the system applies to the display characteristics. For example, the system may initially vary the viewing difficulty so that the perspectives appear equivalent and, then, slowly increase the viewing difficulty of the perspective for the weak viewer-eye. In this way, the system may progressively train the weak viewer-eye to work harder without alerting the viewer of such training. As another example, if a system does not initially vary the complexity of either perspective, then the system may gradually decrease the complexity of the dominant viewer-eye's perspective. Again, such a technique may train the viewer to rely on the weaker eye, without drawing attention to this training As yet another example, a system may initially vary the perspectives in a way that stimulates reliance on the viewer's weak eye (e.g., by increasing the relative viewing difficulty and/or complexity of the weak viewer-eye's perspective) and, then, gradually decreasing the amount of variation that is applied to the display characteristics. Such a technique may help, for instance, to adjust for improvements in the viewer's eyesight. In some cases, the variation may decrease simply by changing in accordance with new eye-strength data as the weak viewer-eye improves. In other cases, the system may follow a preset pattern in decreasing the variation. For example, a system may be programmed to record the amount of time that a viewer uses the training program and adjust the variance in accordance with the total amount of time. Such a technique may be facilitated by the viewer-profile system in that the profile may store historical eye-strength readings and viewing behavior. As another example, a system may be programmed to decrease variation gradually during each viewing session.

In some embodiments, the system may use a periodic cycle of variation. For example, the system may periodically increase and decrease the variation in a sinusoidal, triangle wave, saw-tooth wave, or other periodic pattern. In this way, the system may help prevent a viewer from adjusting to the changes in a way that circumvents the training (e.g., increasing the overall brightness of the screen, moving closer, squinting, etc.) Some cycles may include durations in which no variation is performed or in which the variation causes the viewer to perceive equivalent perspectives. Other time-dependent training techniques are also possible.

The construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. The elements and assemblies may be constructed from any of a wide variety of materials that provide sufficient strength or durability, in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word exemplary is intended to present concepts in a concrete manner. Accordingly, all such modifications are intended to be included within the scope of the present disclosure. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other exemplary embodiments without departing from scope of the present disclosure or from the scope of the appended claims.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

What is claimed is:

1. A method for treating a weak viewer-eye, the method comprising:

detecting a characteristic of the weak viewer-eye from data generated using an eye sensor, wherein the eye sensor is not worn by or coupled to a user;

receiving eye-strength data indicative of an eye-strength of the weak viewer-eye, wherein the eye-strength data is based at least in part on the detected characteristic; and causing an autostereoscopic 3D display system to vary, in accordance with the eye-strength of the weak viewer-eye, display characteristics of a perspective that the autostereoscopic 3D display system displays, wherein the display characteristics are varied in accordance with a time dependent trend of the eye-strength data to predictively adjust the display characteristics in real time while the user is watching the display based on a forward projection of the time dependent trend.

2. The method of claim 1, further comprising generating, at an eye-monitoring system, the eye-strength data.

3. The method of claim 2, wherein generating the eye-strength data comprises using gaze-tracking data to determine the relative eye-strength of the weak viewer-eye with respect to a strong viewer-eye.

4. The method of claim 2, wherein generating the eye-strength data comprises:

tracking the focus of the weak viewer-eye and a corresponding strong viewer-eye; and determining the strength of the weak viewer-eye relative to the strong viewer-eye, based at least in part on the tracked focus.

5. The method of claim 2, wherein generating the eye-strength data comprises monitoring the dilation of the weak viewer-eye to determine the eye-strength of the weak viewer-eye.

6. The method of claim 2, wherein generating the eye-strength data comprises:

using the 3D display system to perform an eye-strength test; and as part of the eye-strength test, receiving user-input indicative of the eye-strength of the weak viewer-eye.

7. The method of claim 2, wherein generating the eye-strength data comprises:

causing the 3D display system to display a first perspective of an image to the weak viewer-eye and a second perspective of the image to a dominant viewer-eye;

receiving an indication regarding a quality of a viewer's perceived 3D effect from the images;

determining, in accordance with the received indication, data associated with the eye-strength of the weak viewer-eye.

8. The method of claim 7, wherein the 3D display system is capable of interfacing with a gaming system, and wherein the received indication comprises a metric of the viewer's game play performance.

9. The method of claim 1, further comprising:

occasionally receiving additional eye-strength data indicative of a current eye-strength of the weak viewer-eye; and causing the 3D display system to vary the display characteristics of the perspective in accordance with the received additional eye-strength data.

10. The method of claim 9, wherein the time dependent trend is identified using the additional eye-strength data, and wherein varying the display characteristics in accordance with the time dependent trend includes a periodic cycle of variation, and wherein the periodic cycle of variation includes at least one of periodically increasing or decreasing the variation in a sinusoidal, triangle wave, and saw-tooth wave pattern.

11. The method of claim 1, wherein causing the 3D display system to vary, in accordance with the eye-strength of the weak viewer-eye, the display characteristics comprises:

evaluating a difference in eye-strength between the weak viewer-eye and a second viewer-eye;

determining whether the evaluated difference in eye-strength is larger than a predefined threshold difference in eye-strength;

in response to determining that the evaluated difference is larger than the threshold difference, causing the 3D display system to vary the display characteristics.

12. The method of claim 11, further comprising:

determining whether the evaluated difference in eye-strength is larger than any of a plurality of predefined threshold differences in eye-strength; and in response to determining that the evaluated difference is larger than a particular set of threshold differences of the plurality of threshold differences, causing the 3D display system to vary the display characteristics in accordance with the particular set of threshold differences.

13. The method of claim 1, wherein varying the display characteristics of the perspective comprises reducing a relative amount of time that a perspective for a dominant viewer-eye is displayed with respect to an amount of time that a perspective for the weak viewer-eye is displayed.

14. The method of claim 1, wherein varying the display characteristics of the perspective comprises reducing, in relative image complexity, a perspective that is displayed to a dominant viewer-eye with respect to an image complexity of a perspective that is displayed to the weak viewer-eye.

15. The method of claim 1, wherein varying the display characteristics of the perspective comprises varying the display characteristics in a way that increases a viewing difficulty of a perspective for the weak viewer-eye with respect to a viewing difficulty of a perspective for a dominant viewer-eye.

16. The method of claim 1, wherein varying the display characteristics of the perspective comprises:

initially varying the display characteristics in a way that decreases a viewing difficulty of a perspective associated with the weak viewer-eye; and increasing the viewing difficulty of the perspective associated with the weak viewer-eye.

17. The method of claim 1, further comprising storing a viewer-profile, wherein the viewer-profile comprises eye-strength data associated with a viewer, and wherein receiving the eye-strength data comprises:

determining that a current viewer is associated with a particular viewer-profile; and loading the eye-strength data associated with the current viewer from the particular viewer-profile.

18. A display-control system comprising:
an eye sensor not worn by or coupled to a user having two viewer-eyes;
a processor;
a computer-readable medium; and
program instructions stored on the computer-readable medium and executable by the processor to cause the processor to:
detect a characteristic of a weak viewer-eye from data generated using the eye sensor;
receive eye-strength data representative of an eye-strength of each of the two viewer-eyes, wherein one of the viewer-eyes is a weak viewer-eye, wherein the eye-strength data of the weak-viewer eye is based at least in part on the detected characteristic; and
cause an autostereoscopic 3D display system to vary, in accordance with an eye-strength of the weak viewer-eye, display characteristics of a perspective that the autostereoscopic 3D display system displays on the display screen,
wherein the program instructions are further executable to cause the eye-monitoring system to generate the eye-strength data, and
wherein generating the eye-strength data comprises: causing the autostereoscopic 3D display system to display a first perspective of an image to the weak viewer-eye and a second perspective of the image to a dominant viewer-eye;
receiving an indication regarding a quality of a viewer's perceived 3D effect from the images;
determining, in accordance with the received indication, data associated with the eye-strength of the weak viewer-eye, and
wherein the autostereoscopic 3D display system is capable of interfacing with a gaming system, and wherein the received indication comprises a metric of the viewer's game play performance.

19. The display-control system of claim 18, wherein the program instructions are further executable to cause an eye-monitoring system to generate the eye-strength data, and wherein generating the eye-strength data comprises using gaze-tracking data to determine the relative eye-strength of the weak viewer-eye with respect to a second viewer-eye.

20. The display-control system of claim 18, wherein the program instructions are further executable to cause the eye-monitoring system to generate the eye-strength data, and wherein generating the eye-strength data comprises:
using the 3D display system to perform an eye-strength test; and
as part of the eye-strength test, receiving user-input indicative of the eye-strength of the weak viewer-eye.

21. The display-control system of claim 18, wherein the 3D display system comprises a portable device.

22. The display-control system of claim 18, wherein varying the display characteristics of the perspective comprises decreasing a relative brightness of a perspective that is displayed to the weak viewer-eye with respect to a brightness of a perspective that is displayed to a dominant viewer-eye.

23. The display-control system of claim 18, wherein varying the display characteristics of the perspective comprises reducing a relative amount of time that a perspective for a dominant viewer-eye is displayed with respect to an amount of time that a perspective for the weak viewer-eye is displayed.

24. The display-control system of claim 18, wherein varying the display characteristics of the perspective comprises reducing, in relative image complexity, a perspective that is displayed to a dominant viewer-eye with respect to an image complexity of a perspective that is displayed to the weak viewer-eye.

25. The display-control system of claim 18, wherein varying the display characteristics of the perspective comprises varying the display characteristics in a way that increases a viewing difficulty of a perspective for the weak viewer-eye with respect to a viewing difficulty of a perspective for a dominant viewer-eye.

26. The display-control system of claim 18, wherein varying the display characteristics of the perspective comprises varying the display characteristics in a way that decreases a viewing difficulty of a perspective associated with the weak viewer-eye, with respect to a previous viewing difficulty.

27. The display-control system of claim 18, wherein varying the display characteristics of the perspective comprises:
initially varying the display characteristics in a way that decreases a viewing difficulty of a perspective associated with the weak viewer-eye; and
gradually increasing the viewing difficulty of the perspective associated with the weak viewer-eye;
wherein the display characteristics of the perspective are varied in real time while the user is watching the display.

28. The display-control system of claim 18, wherein the program instructions are further executable to cause the processor to store a viewer-profile in the computer-readable medium, wherein the viewer-profile comprises eye-strength data associated with a viewer, and wherein receiving the eye-strength data comprises:
determining that a current viewer is associated with a particular viewer-profile; and
loading the eye-strength data associated with the current viewer from the particular viewer-profile.

29. A non-transitory computer-readable medium having stored thereon program instructions executable by a processor to cause a display-control device to:
detect a characteristic of two or more viewer-eyes from data generated using an eye sensor, wherein the eye sensor is not worn by or coupled to a user;
receive eye-strength data representative of an eye-strength of the two or more viewer-eyes, wherein the eye-strength data is indicative of one of the two or more viewer-eyes being a weak viewer-eye, and wherein the eye-strength data is based at least in part on the detected characteristic; and
cause an autostereoscopic 3D display system to vary, in accordance with the eye strength of the weak viewer-eye, display characteristics of the perspective that the autostereoscopic 3D display system displays, wherein the display characteristics are varied by reducing the rate at which frames change for one perspective, and wherein reducing the rate at which frames change for one perspective includes displaying each frame for the one perspective for twice the normal duration and refraining from displaying every other frame of the one perspective, wherein varying the display characteristics of the perspective comprises:
initially varying the display characteristics in a way that decreases a viewing difficulty of a perspective associated with the weak viewer-eye; and
gradually increasing the viewing difficulty of the perspective associated with the weak viewer-eye;
wherein the display characteristics of the perspective are varied in real time while the user is watching the display.

30. The computer-readable medium of claim 29, wherein the eye-strength data is received from an integral eye-monitoring system, and wherein the program instructions are further executable to cause the integral eye-monitoring system to generate the eye-strength data.

31. The computer-readable medium of claim 30, wherein generating the eye-strength data comprises using gaze-tracking data to determine the relative eye-strength of the weak viewer-eye with respect to a second viewer-eye.

32. The computer-readable medium of claim 30, wherein generating the eye-strength data comprises:
    causing the 3D display system to display a first perspective of an image to the weak viewer-eye and a second perspective of the image to a dominant viewer-eye;
    receiving an indication regarding a quality of a viewer's perceived 3D effect from the images, wherein the 3D display system is capable of interfacing with a gaming system, and wherein the received indication comprises a metric of the viewer's game play performance; and
    determining, in accordance with the received indication, data associated with the eye-strength of the weak viewer-eye.

33. The computer-readable medium of claim 29, wherein varying the display characteristics of the perspective comprises varying the display characteristics in a way that increases a viewing difficulty of a perspective for the weak viewer-eye with respect to a viewing difficulty of a perspective for a dominant viewer-eye.

34. The computer-readable medium of claim 29, wherein the program instructions are further executable to cause the display-control device to store a viewer-profile, wherein the viewer-profile comprises eye-strength data associated with a viewer, and wherein receiving the eye-strength data comprises:
    determining that a current viewer is associated with a particular viewer-profile; and
    loading the eye-strength data associated with the current viewer from the particular viewer-profile.

* * * * *